(12) United States Patent
Stocker et al.

(10) Patent No.: US 6,936,610 B2
(45) Date of Patent: *Aug. 30, 2005

(54) HETEROCYCLIC DERIVATIVES

(75) Inventors: Andrew Stocker, Macclesfield (GB); John Preston, Macclesfield (GB); John Wall Rayner, Macclesfield (GB); Michael James Smithers, Macclesfield (GB); Paul Turner, Macclesfield (GB)

(73) Assignee: AstraZeneca UK Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/963,686

(22) Filed: Sep. 27, 2001

(65) Prior Publication Data

US 2003/0195203 A1 Oct. 16, 2003

Related U.S. Application Data

(63) Continuation of application No. 09/297,768, filed as application No. PCT/GB97/03033 on Nov. 4, 1997, now Pat. No. 6,300,330.

(30) Foreign Application Priority Data

Nov. 8, 1996 (GB) .............................................. 9623283
Jul. 29, 1997 (GB) .............................................. 9715893

(51) Int. Cl.[7] ...................... A61K 31/496; C07D 401/10
(52) U.S. Cl. ............................ 514/252.02; 514/253.02; 514/253.12; 514/254.14; 544/238; 544/295; 544/360
(58) Field of Search ................................ 544/238, 295, 544/360; 514/252.02, 253.02, 253.17, 254.14

(56) References Cited

U.S. PATENT DOCUMENTS

| | | | |
|---|---|---|---|
| 4,167,567 A | 9/1979 | McCall ........................ 424/273 |
| 4,231,938 A | 11/1980 | Monaghan et al. ...... 260/343.5 |
| 4,537,896 A | 8/1985 | Claeson et al. ............. 514/330 |
| 4,564,610 A | 1/1986 | Rahtz et al. ................... 514/80 |
| 4,629,728 A | 12/1986 | Regnier et al. .............. 514/252 |
| 4,788,196 A | 11/1988 | Cross et al. ................. 514/252 |
| 4,806,536 A | 2/1989 | Cross et al. ................. 514/252 |
| 4,835,165 A | 5/1989 | Cross et al. ................. 514/318 |
| 4,840,963 A | 6/1989 | Shepard et al. ............. 514/418 |
| 4,968,704 A | 11/1990 | Cross et al. ................. 514/318 |
| 5,032,604 A | 7/1991 | Baldwin et al. ............. 514/361 |
| 5,138,058 A | 8/1992 | Geisen et al. ............... 544/295 |
| 5,254,563 A | 10/1993 | Huth et al. .................. 514/292 |
| 5,332,822 A | 7/1994 | Misra .......................... 546/164 |
| 5,364,865 A | 11/1994 | Diana .......................... 514/318 |
| 5,371,091 A | 12/1994 | Misra et al. ................. 514/314 |
| 5,411,971 A | 5/1995 | Emonds-Alt et al. ....... 514/318 |
| 5,556,977 A | 9/1996 | Wayne et al. ............... 544/360 |
| 5,563,141 A | 10/1996 | Wayne et al. ............... 514/252 |
| 5,580,881 A | 12/1996 | Binet et al. .................. 514/307 |
| 5,606,065 A | 2/1997 | Emonds-Alt et al. ....... 546/223 |
| 5,681,954 A | 10/1997 | Yamamoto et al. ......... 544/114 |
| 5,795,893 A | 8/1998 | Bondinell et al. .......... 514/254 |
| 5,856,326 A | 1/1999 | Anthony et al. ............ 514/252 |
| 6,022,869 A | 2/2000 | Faull ....................... 514/227.8 |
| 6,037,343 A | 3/2000 | Ali .............................. 514/252 |

FOREIGN PATENT DOCUMENTS

| | | |
|---|---|---|
| AU | 10177/92 | 7/1992 |
| DE | 39 05 364 A1 | 8/1990 |
| DE | 39 43 225 A | 6/1991 |
| DE | 42 43 858 A1 | 6/1994 |
| DE | 43 06 506 A1 | 9/1994 |
| EP | 0 097 630 A2 | 1/1984 |
| EP | 0 232 740 A1 | 8/1987 |
| EP | 0 233 051 | 8/1987 |
| EP | 0 244 115 | 11/1987 |
| EP | 0 324 421 A2 | 7/1989 |
| EP | 0 308 337 | 9/1989 |
| EP | 0 352 946 A1 | 1/1990 |
| EP | 0 359 389 | 3/1990 |
| EP | 0 409 413 | 1/1991 |
| EP | 0 495 750 | 7/1992 |
| EP | 0 515 240 A1 | 11/1992 |
| EP | 0 519 449 A1 | 12/1992 |
| EP | 0 555 824 A1 | 8/1993 |
| EP | 0 576 941 A1 | 1/1994 |
| EP | 0 608 759 A2 | 8/1994 |
| FR | 2 697 252 A1 | 4/1994 |
| GB | 1 449 100 | 7/1976 |
| WO | 92/08706 | 5/1992 |
| WO | 92/18478 | 10/1992 |
| WO | 93/06085 | 4/1993 |
| WO | 94/18185 | 8/1994 |
| WO | 94/20467 | 9/1994 |
| WO | 94/20468 | 9/1994 |

(Continued)

OTHER PUBLICATIONS

Boissier et al., "Synthesis and Pharmacological Study of New Piperazine Derivatives . . . Benzylpiperazines", J. Med. Chem., Sep. 1963, pp. 541–544.

(Continued)

Primary Examiner—Richard L. Raymond
(74) Attorney, Agent, or Firm—Morgan, Lewis & Bockius LLP

(57) ABSTRACT

The invention relates to heterocyclic derivatives of formula (I)

$$A—B—X^1—T^1(R^2)—L^1—T^2(R^3)—X^2—Q \qquad (I)$$

or pharmaceutically-acceptable salts thereof, which possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

11 Claims, No Drawings

FOREIGN PATENT DOCUMENTS

| WO | 94/22835 | 10/1994 |
|---|---|---|
| WO | 96/05189 | 2/1996 |
| WO | 96/10022 | 4/1996 |
| WO | 96/26196 | 8/1996 |
| WO | 96/30343 | 10/1996 |
| WO | 96/33171 | 10/1996 |
| WO | 97/06802 | 2/1997 |
| WO | 97/28128 | 8/1997 |
| WO | 97/28129 | 8/1997 |
| WO | 97/29104 | 8/1997 |
| WO | 97/30971 | 8/1997 |
| WO | 98/06705 | 2/1998 |
| WO | 9/21188 | 5/1998 |

OTHER PUBLICATIONS

Bowers Nemia et al., "Synthetic Routes to 3–Pyrrolidinol", Synth. Comm. 13(13):1117–1123 (1983).

Budavari: Merck Index, vol. 11 ED., 1989, See Monograph Nos. 804 and 2807.

Cattel et al., "Drug design based on biosynthetic studies: synthesis, biological activity, and kinetics of new inhibitors of 2,3–oxidosqualene cyclase and squalene epoxidase", Steroids, vol. 53, No. 3–5, 1989, pp. 363–391, XP000611661.

Caulkett et al., Chemical Abstracts. vol. 131:322629, 1999.

Chambers et al., "Preparation of arylpyridine compounds for treating leukotriene–related diseases", Chemical Abstracts, Abstract No. 139113, vol. 119 (1993).

Conway et al., "Approaches to the Generation of 2,3–Indolyne", Heterocycles, 1992, 34(11) pp. 2095–2108.

Cross et al., "Preparation of N–[(hetrocyclicylmethoxy)phenyl] sulfamides and analogs as antiarrhythmics", Chemical Abstracts, Abstract No. 231211, vol. 113 (1989).

Deratani et al., "Synthesis of new dialkylaminopyridine acylation catalysts and their attachment to insoluble polymer supports", Polymer, Apr. 1987, pp. 825–830.

Jucker, "Über C–substituierte Piperazinderativate", Helv. Chim. Acta., 45:2383–2042 (1962).

Hibino et al., "N–Phenysulfonylindole derivatives", Chemical Abstracts, 118:147461, Apr., 1993.

Jain et al., "Compounds Acting on the Central Nervous System, VII. Studies in 1–Pyridyl–1–substituted Piperazines. A New Class of Anticonvulsants", J. Med. Chem., Sep. 1967, pp. 812–818.

Kataoka et al., Chemical Abstracts, vol. 123, No. 14, Oct. 2, 1995, Columbus, Ohio, U.S.; Abstract No. 179521d, "Homopiperazines as cell migration inhibitors", XP002081582, see abstract & JP 95 145060 A (Tejin Ltd).

Kato et al., "Reactivities of 4–Chloropyridine Derivatives and Their 1–Oxides", Chem. Pharm. Bull., 15:1343–1348 (1967).

Kato et al., "Studies on Ketene and Its Derivatives. LXXVI. $^{1)}$Reactions of Acetoacetamide and β–Aminocrotonamide and β–Diketone, β–Ketoaldehyde and Related Compounds", Chem. Pharm. Bull., 24(2):303–309 (1976).

Kobayashi et al., Chemical Abstracts, vol. 132:194391, 2000.

Mitsunobu et al., "Preparation of Carboxylic Esters and Phosphoric Esters by the Activation of Alcohols", Bull. Chem. Soc. Jpn., 44(12):3427–3430 (1971).

Nowak et al., Chemical Abstracts, vol. 131:337034, 1999.

Kettner et al., "The Selective Inhibition of Thrombin by Peptides of Boroarginine", The Journal of Biological Chemistry, vol. 265, No. 30, pp. 18289–18297 (1990).

Kobayashi et al., Chemical Abstracts, vol. 130:296694, 1999.

Prasad et al., "Antiamoebic Action of Drugs and Synthetic Compounds Against Trophozoites of *Entamoeba histoltica* Under Axenic and Polyxenic Culture Conditions and in the Infected Rat Caecum", Curr. Sci., Aug. 1984, pp. 778–781.

Ratouis et al., "Synthesis and Pharmacological Study of New Piperazine Derivatives, II. Phenethylpiperazines", J. Med. Chem., Jan. 1965, pp. 104–107.

Sartori et al., "Synthesis and analgesic activities of urea derivatives of $_\alpha$–amino–N–pyridyl benzene propanamide", Eur J. Med Chem (1994), pp. 431–439.

Sato et al., "Synthetic Studies on Cardiovascular Agents. III. Synthesis of Pyrano–[2,3–c]pyrazoline Derivatives", Yakugaku Zasshi, vol. 98(3), 1978, pp. 335–348.

Saxena et al., "Quantitative Structure Activity Realtionship in 3–4 Disubstituted Pyridines & 1–(3"–Amino–4"pyridyl)–4–arylpiperazines", Indian J. Chem., vol. 19B, Oct., 1980, pp. 873–878.

Smith et al., "Fibrin, Red Cell and Platelet Interactions in an Experimental Model of Thrombosis", Br. J. Pharmac., vol. 77, pp. 29–38 (1982).

Sundberg et al., "Synthesis with N–Protected 2–Lithioindoles", J. Org. Chem., 1973, 38(19) 3324–3330.

Szmant et al., "Concerning the Variable Character of the Sulfone Group", J. Amer. Chem. Soc., vol. 78, pp. 3400–3403 (1956).

Tabacik et al., "Squalene expoxidase, oxido–squalene cyclase and cholesterol biosynthesis in normal and tumoral mucosa of the human gastrointestinal tract. Evidence of post–HMGACoA regulation", Biochim. Biophys. Acta, vol. 666, No. 3, 1982, pp. 433–441, XP000610864.

Take et al., Chemical Abstracts, vol. 133:58814, 2000.

Tawada et al., Chemical Abstracts, vol. 130:38404, 1998.

Tawada et al., Chemical Abstracts, vol. 131:170361, 1999.

Vigroux et al., "Cyclization–Activated Prodrugs: N–(Substituted 2–hydroxyphenyl and 2–hydroxypropyl)carbamates Based on Ring–Opened Derivatives of Active Benzoxazolones and Oxazolidones as Mutual Prodrugs of Acetamiophen", J. Med. Chem., vol. 38, pp. 3983–3994 (1995).

Vogel et al., "Cpmparison of TExperimental Thrombosis Models In Rats Effects of Four Glycosaminoglycans", Thrombosis Research, vol. 54, No. 5, pp. 399–410 (1989).

Von G. Krüger, et al., "(Thomae et al.) Arzneim.–Forsch., Synthesen von N–Benzyl–aminocarbonsäuren und thren Derivaten", (Synthesis and N–benzylaminocarboxylic acids and their derivatives), vol. 23(2a), pp. 290–295, 1973.

Wallis, "Inhibitors of Coagulation Factor Xa: From Macromolecular Beginnings to Small Molecules", Current Opinion in Therapeutic Patents, Aug., 1993, pp. 1173–1179.

Yokoyama et al., "Palladium–catalyzed cross–coupling reaction: direct allylation of aryl bromides with allyl acetate", Tetrahedron Letters, vol. 26, No. 52, 195, pp. 6457–6460, XP002081581 Oxford GB, pp. 6458–64569: compound 7, 1985.

Zagral et al., "Amino acids and peptides. LIX. Synthesis and some biological properties of L–DABB–vasopressin", Collec. Czech. Chem. Commun., vol. 31, 1966, pp. 90–95, XP002081879, see compound 11, p. 95.

HETEROCYCLIC DERIVATIVES

This application is a continuation of application Ser. No. 09/297,768, filed May 7, 1999, now U.S. Pat. No. 6,300,330, which is a 371 of PCT/GB97/03033, filed Nov. 4, 1997.

The invention relates to heterocyclic derivatives, or pharmaceutically-acceptable salts thereof, which possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis, *Current Opinion in Therapeutic Patents*, 1993, 1173–1179. Thus it is known that two proteins, one known as antistatin and the other known as tick anticoagulant protein (TAP), are specific Factor Xa inhibitors which possess antithrombotic properties in various animal models of thrombotic disease.

It is also known that certain non-peptidic compounds possess Factor Xa inhibitory properties. Of the low molecular weight inhibitors mentioned in the review by R. B. Wallis, all possessed a strongly basic group such as an amidinophenyl or amidinonaphthyl group.

We have now found that certain heterocyclic derivatives possess Factor Xa inhibitory activity. Many of the compounds of the present invention also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

PCT International Publication Number WO9610022 describes certain heterocyclic piperazine compounds as Factor Xa inhibitors. PCT International Publication Number WO9728129, published after the priority date of this application, describes also certain heterocyclic piperazine compounds as Factor Xa inhibitors. PCT International Publication Number WO9730971, published after the priority date of this application, discloses benzamidine type compounds as Factor Xa inhibitors.

The compounds of the present invention possess activity in the treatment or prevention of a variety of medical disorders where anticoagulant therapy is indicated, for example in the treatment or prevention of thrombotic conditions such as coronary artery and cerebro-vascular disease. Further examples of such medical disorders include various cardiovascular and cerebrovascular conditions such as myocardial infarction, the formation of cerebro-vascular disease. Further examples of such medical disorders include various cardiovascular and cerebrovascular conditions such as myocardial infarction, the formation of atherosclerotic plaques, venous or arterial thrombosis, coagulation syndromes, vascular injury including reocclusion and restenosis following angioplasty and coronary artery bypass surgery, thrombus formation after the application of blood vessel operative techniques or after general surgery such as hip replacement surgery, the introduction of artificial heart valves or on the recirculation of blood, cerebral infarction, cerebral thrombosis, stroke, cerebral embolism, pulmonary embolism, ischaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

Accordingly in one aspect the present invention provides compounds of formula (I)

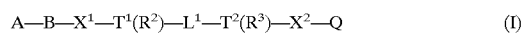

A—B—X¹—T¹(R²)—L¹—T²(R³)—X²—Q    (I)

wherein:

A is an optionally substituted 5- or 6-membered monocyclic aromatic ring containing 1, 2 or 3 ring heteroatoms selected from nitrogen, oxygen and sulphur atoms;
B is an optionally substituted phenylene ring;
$T^1$ is CH or N;
$T^2$ is CH or N;
with the proviso that at least one of $T^1$ and $T^2$ is N;
$X^1$ is SO, $SO_2$, $C(R^4)_2$ or CO when $T^1$ is CH or N; or in addition $X^1$ is O or S when $T^1$ is CH;
and wherein each $R^4$ is independently hydrogen or $C_{1-4}$alkyl;
$L^1$ is $C_{1-4}$ alkylene or $C_{1-3}$alkylenecarbonyl;
$R^2$ is hydrogen or $C_{1-4}$alkyl;
$R^3$ is hydrogen or $C_{1-4}$alkyl;
or $R^2$ and $R^3$ are joined to form a $C_{1-4}$alkylene or —$CH_2CO$— group; wherein the ring formed by $T^1$, $R^2$, $R^3$, $T^2$ and $L^1$ is optionally substituted; with the proviso that when $T^1$ and $T^2$ are both N, $L^1$ is not methylene and $R^2$ and $R^3$ together are not methylene;
$X^2$ is $S(O)_y$ wherein y is one or two, $C(R^5)_2$ or CO; and each $R^5$ is hydrogen or $C_{1-4}$alkyl;
Q is phenyl naphthyl, phenyl$C_{1-4}$alkyl, phenyl$C_{2-4}$alkenyl, phenyl$C_{2-4}$alkynyl or a heterocyclic moiety containing up to 4 heteroatoms selected from nitrogen, oxygen and sulphur and Q is optionally substituted;
and pharmaceutically acceptable salts thereof.

In this specification the term "alkyl" includes both straight and branched chain alkyl groups but references to individual alkyl groups such as "propyl" are specific, for the straight chain version only. An analogous convention applies to other generic terms.

It is to be understood that certain heterocyclic derivatives of the present invention can exist in solvated as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

A is an optionally substituted 5- or 6-membered monocyclic aromatic ring containing 1, 2 or 3 ring nitrogen atoms. Preferably A is a pyridyl, pyrimidinyl or pyridazinyl ring for example 4-pyridyl, 2-pyridyl, 4-pyridazinyl, 5-pyrimidinyl, 4-pyrimidinyl or 3-pyridyl. Of these 4-pyrimidinyl, 4-pyridazinyl and 4-pyridyl are preferred of which 4-pyrimidinyl and 4-pyridyl are most preferred.

In one aspect A is unsubstituted. In another aspect A is substituted by one, two or three atoms or groups selected from halo (for example fluoro, chloro or bromo), oxo, carboxy, trifluoromethyl, cyano, amino, hydroxy, nitro, $C_{1-4}$alkyl (for example methyl or ethyl), $C_{1-4}$alkoxy (for example methoxy or ethoxy), $C_{1-4}$alkoxycarbonyl, $C_{1-4}$alkylamino (for example methylamino or ethylamino) or di-$C_{1-4}$alkylamino (for example dimethylamino or diethylamino). For the avoidance of doubt susbstituents on A may also be present, where possible, on the heteroatom of the ring, such as, for example, N-oxides. Preferred substituents are $C_{1-4}$alkyl and halo. Preferably A is unsubstituted B is an optionally substituted phenylene ring wherein the bonds to A and $X^1$ may suitably be in the meta or para disposition. Preferably the bonds to A and $X^1$ are in para dispostion, that is B is a para-phenylene group.

In one aspect B is unsubstituted. In another aspect B is substituted by one or two substituents selected from halo, trifluoromethyl, trifluoromethoxy, cyano, nitro, $C_{1-4}$alkyl, $C_{2-4}$alkenyl and $C_{2-4}$alkynyl, from the substituent —$(CH_2)_n$Y$^1$ wherein n is 0–4 and Y$^1$ is selected from hydroxy, amino, carboxy, $C_{1-4}$alkoxy, $C_{2-4}$alkenyloxy, $C_{2-4}$alkynyloxy, $C_{1-4}$alkylamino, di-$C_{1-4}$alkylamino, pyrrolidin-1-yl, piperidino, morpholino, thiomorpholino, 1-oxothiomorpholino, 1,1-dioxothiomorpholino, piperazin-1-yl, 4-$C_{1-4}$alkylpiperazin-1-yl, $C_{1-4}$alkylthio, $C_{1-4}$alkylsulphinyl, $C_{1-4}$alkylsulphonyl. $C_{2-4}$alkanoylamino, benzamido, $C_{1-4}$alkylsulphonamido and phenylsulphonamido, from the substituent —$(CH_2)_nY^2$ wherein n is 0–4 and Y$^2$ is selected from carboxy, carbamoyl. $C_{1-4}$alkoxycarbonyl,N—$C_{1-4}$alkylcarbamoyl, N,N-di-$C_{1-4}$alkylcarbamoyl, pyrrolidin-1-ylcarbonyl, piperidinocarbonyl, morpholinocarbonyl, thiomorpholinocarbonyl, 1-oxothiomorpholinocarbonyl, 1,1-dioxothiomorpholinocarbonyl, piperazin-1-ylcarbonyl, 4-$C_{1-4}$alkylpiperazin-1-ylcarbonyl, $C_{1-4}$alkylsulphonamidocarbonyl, phenylsulphonamidocarbonyl and benzylsulphonamidocarbonyl, from a substituent of the formula —$X^3$-$L^2$—$Y^2$ wherein $X^3$ is a group of the formula CON($R^5$), CON($L^2$—$Y^2$) C($R^5$)$_2$O, O, N($R^5$) or N($L^2$—$Y^2$), $L^2$ is $C_{1-4}$alkylene, $Y^2$ has any of the meanings defined immediately hereinbefore and each $R^5$ is independently hydrogen or $C_{1-4}$alkyl, and from a substituent of the formula —$X^3$—$L^3$—$Y^1$ wherein $X^3$ is a group of the formula CON($R^5$), CON($L^3$—$Y^1$), C($R^5$)$_2$O, O, N($R^5$) or N($L^3$—$Y^1$), $L^3$ is $C_{2-4}$alkylene, $Y^1$ has any of the meanings defined immediately hereinbefore and each $R^5$ is independently hydrogen or $C_{1-4}$alkyl, and wherein any heterocyclic group in a substituent of B optionally bears 1 or 2 substituents selected from carboxy, carbamoyl, $C_{1-4}$alkyl, $C_{1-4}$alkoxycarbonyl, N—$C_{1-4}$alkylcarbamoyl and N,N-di-$C_{1-4}$alkylcarbamoyl, and wherein any phenyl group in a substituent of B optionally bears 1 or 2 substituents selected from halo, trifluoromethyl, cyano, $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy. Preferably B is substituted by carboxy, $C_{1-4}$alkoxy or $C_{1-4}$alkoxycarbonyl. Preferably B is unsubstituted.

In a particular aspect, when T$^1$ is CH or N, X$^1$ is CO, SO$_2$, or CH$_2$ or, when T$^1$ is CH, X$^1$ in addition is O or S. Preferably X$^1$ is CO.

For the avoidance of doubt T$^1$ is directly attached to the groups X$^1$ and L$^1$ and T$^2$ is directly attached to the groups L$^1$ and X$^2$.

L$^1$ is $C_{1-4}$alkylene for example methylene, ethylene or propylene (preferably ethylene) or is $C_{1-3}$alkylenecarbonyl for example methylenecarbonyl (—CH$_2$CO—).

R$^2$ is hydrogen or $C_{1-4}$alkyl for example methyl or ethyl. R$^3$ is hydrogen or $C_{1-4}$alkyl for example methyl or ethyl.

In a preferred aspect R$^2$ and R$^3$ are joined to form a $C_{1-4}$alkylene group, for example a methylene, ethylene or propylene group (preferably ethylene), or a methylenecarbonyl (—CH$_2$CO—) group.

In a particular aspect R$^2$ and R$^3$ are joined to form, together with T$^1$, T$^2$ and L$^1$, a heterocyclic ring wherein at least one of T$^1$ and T$^2$ is N. Examples of such heterocyclic rings are piperazine (wherein T$^1$ and T$^2$ are both N), piperidine (wherein either T$^1$ or T$^2$ is N and the other is CH) and pyrrolidine (wherein either T$^1$ or T$^2$ is N and other is CH). Preferably the heterocyclic ring formed by R and R$^1$ is piperazine.

In one aspect the heterocyclic ring formed by T$^1$, T$^2$, L$^1$, R$^2$ and R$^3$ is unsubstituted. In another aspect this ring is substituted by one or two substituents selected from hydroxy, oxo, carboxy and $C_{1-4}$alkoxycarbonyl; or one of the following:

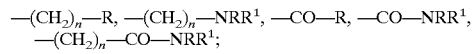

wherein n is 0, 1 or 2, preferably n is 1 or 2;
R and R$^1$ are independently selected from hydrogen, $C_{1-4}$alkyl, $C_{2-4}$alkenyl, $C_{2-4}$alkynyl, hydroxy$C_{1-4}$alkyl, carboxy$C_{1-4}$alkyl and $C_{1-4}$alkoxycarbonyl$C_{1-4}$alkyl or where possible R and R$^1$ may together form a 5- or 6-membered optionally substituted saturated or partially unsaturated (preferably saturated) heterocyclic ring which may include in addition to the nitrogen to which R and R$^1$ are attached 1 or 2 additional heteroatoms selected from nitrogen, oxygen and sulphur.

In a particular aspect the heterocyclic ring formed by R and R$^1$ are preferably selected from 1-pyrrolidinyl, 1-imidazolinyl, 1-piperidino, 1-piperazinyl, 4-morpholino and 4-thiomorpholino. In a particular aspect the heterocyclic ring formed by R and R$^1$ may be unsubstituted. In an alternative aspect the ring formed by R and R$^1$ is substituted by 1 or 2 substituents selected from oxo, hydroxy and carboxy. Preferably the heterocyclic ring formed by T$^1$, T$^2$, L$^1$, R$^2$ and R$^3$ is substituted by oxo, carboxy, $C_{1-4}$alkoxy or $C_{1-4}$alkoxycarbonyl. Preferably the heterocyclic ring formed by T$^1$, T$^2$, L$^1$, R$^2$ and R$^3$ is unsubstituted.

In a particular aspect X$^2$ is SO$_2$, CH$_2$ or CO. Preferably X$^2$ is SO$_2$.

In one aspect Q is unsubstituted. In another aspect Q is substituted by one, two or three substituents selected from halo, trifluromethyl, trifluoromethoxy, cyano, hydroxy, amino, nitro, trifluoromethylsulphonyl, carboxy, carbamoyl, $C_{1-4}$alkyl, $C_{2-4}$alkenyl, $C_{2-4}$alkynyl, $C_{1-4}$alkoxy, $C_{2-4}$alkenyloxy, $C_{2-4}$alkynyloxy, $C_{1-4}$alkylthio, $C_{1-4}$alkylsulphinyl, $C_{1-4}$alkylsulphonyl, $C_{1-4}$alkylamino, di-$C_{1-4}$alkylamino, $C_{1-4}$alkoxycarbonyl, N—$C_{1-4}$alkylcarbamoyl, N,N-di-$C_{1-4}$alkylcarbamoyl, $C_{2-4}$alkanoyl, $C_{2-4}$alkanoylamino, hydroxy$C_{1-4}$alkyl, $C_{1-4}$alkoxy$C_{1-4}$alkyl, carboxy$C_{1-4}$alkyl, $C_{1-4}$alkoxycarbonyl$C_{1-4}$alkyl, carbamoyl$C_{1-4}$alkyl, N—$C_{1-4}$alkylcarbamoyl$C_{1-4}$alkyl, N,N-di-$C_{1-4}$alkylcarbamoyl$C_{1-4}$alkyl, phenyl, heteroaryl, phenoxy phenylthio, phenylsulphinyl, phenylsulphonyl, benzyl, benzoyl, heteroaryloxy, heteroarylthio, heteroarylsulphinyl and heteroarylsulphonyl, and wherein said heteroaryl substituent or the heteroaryl group in a heteroaryl-containing substituent is a 5- or 6-membered monocyclic heteroaryl ring containing up to 3 heteroatoms selected from nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2 or 3 substituents selected from halo, trifluoromethyl, cyano, hydroxy, amino, nitro, carboxy, carbamoyl, $C_{1-4}$alkyl, $C_{1-4}$alkoxy, $C_{1-4}$alkylamino, di-$C_{1-4}$alkylamino, $C_{1-4}$alkoxycarbonyl, N—$C_{1-4}$alkylcarbamoyl, N,N-di-$C_{1-4}$alkylcarbamoyl and $C_{2-4}$alkanoylamino.

A suitable value for Q when it is naphthyl is, for example, 1-naphthyl or 2-naphthyl; when it is phenyl-$C_{1-4}$alkyl is, for example, benzyl, phenethyl and 3-phenylpropyl, when it is phenyl-$C_{2-4}$alkenyl is, for example, styryl, cinnamyl or 3-phenylprop-2-enyl; and when it is phenyl-$C_{2-4}$alkynyl is, for example, 2-phenylethynyl, 3-phenylprop-2-ynyl and 3-phenylprop-1-ynyl. Preferably Q is naphthyl in particular 2-naphthyl.

A suitable value for Q when it is a heterocyclic moiety containing up to 4 heteroatoms selected from nitrogen, oxygen and sulphur is, for example, a 5- or 6-membered heterocyclic moiety which is a single ring or is fused to one or two benzo rings such as furyl, benzofuranyl, tetrahydrofuryl, chromanyl, thienyl, benzothienyl, pyridyl, piperidino, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imidazolyl, benzimidazolyl, pyrazolyl, indazolyl, oxazolyl, benzoxazolyl, isoxazolyl, thiazolyl, benzothiazolyl, isothiazolyl, morpholino, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl and dibenzothienyl, which may be attached through any available position including, for an appropriate $X^2$ group such as, for example, $SO_2$, $C(R^5)_2$ or CO, through any available nitrogen atom, and which may bear up to three substituents as defined hereinabove including a substituent on any available nitrogen atom.

A suitable value for the heteroaryl substituent on Q or the heteroaryl group in a heteroaryl-containing substituent on Q which comprises a 5- or 6-membered monocyclic heteroaryl ring containing up to 3 heteroatoms selected from oxygen, nitrogen and sulphur is, for example, furyl, thienyl, pyridyl, pyrazinyl, pyrimidinyl, pyridazinyl, pyrrolyl, imidazolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached through any available position including, for an appropriate $X^2$ group such as, for example, $SO_2$, $C(R^5)_2$ or CO, through any available nitrogen atom, and which may be up to three substituents as defined hereinabove including a substituent on any available nitrogen atom.

Suitable values for optional substituents for B and Q are:

for $C_{1-4}$alkyl: methyl, ethyl and propyl;
for $C_{1-4}$alkoxycarbonyl: methoxycarbonyl, ethoxycarbonyl, propoxycarbonyl and tert-butoxycarbonyl;
for N—$C_{1-4}$alkylcarbamoyl: N-methylcarbamoyl, N-ethylcarbamoyl and N-propylcarbamoyl;
for N,N-di-$C_{1-4}$alkylcarbamoyl: N,N-dimethylcarbamoyl, N-ethyl-N-methylcarbamoyl and N,N-diethylcarbamoyl;
for hydroxy$C_{1-4}$alkyl: hydroxymethyl, 1-hydroxyethyl, 2-hydroxyethyl and 3-hydroxypropyl;
for $C_{1-4}$alkoxy$C_{1-4}$alkyl: methoxymethyl, ethoxymethyl, 1-methoxymethyl, 2-methoxyethyl, 2-ethoxyethyl and 3-methoxypropyl;
for carboxy$C_{1-4}$alkyl: carboxymethyl, 1-carboxyethyl, 2-carboxyethyl and 3-carboxypropyl;
for $C_{1-4}$alkoxycarbonyl$C_{1-4}$alkyl: methoxycarbonylmethyl, ethoxycarbonylmethyl, tert-butoxy-carbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl;
for carbamoyl$C_{1-4}$alkyl: carbamoylmethyl, 1-carbamoylethyl, 2-carbamoylethyl and 3-carbamoylpropyl;
for N—$C_{1-4}$alkylcarbamoyl$C_{1-4}$alkyl: N-methylcarbamoylmethyl, N-ethylcarbamoylmethyl, N-propylcarbamoylmethyl, 1-(Nmethylcarbamoyl)ethyl, 1-(Nethylcarbarnoyl)ethyl, 2-(Nmethylcarbamoyl)ethyl, 2-(Nethylcarbamoyl)ethyl and 3-(Nmethylcarbamoyl)propyl;
for N,N-di-$C_{1-4}$alkylcarbamoyl-$C_{1-4}$alkyl: N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl;
for halo: fluoro, chloro, bromo;
for $C_{1-4}$alkoxy: methoxy, ethoxy;
for $C_{1-4}$alkylamino: methylamino, ethylamino;
for di-$C_{1-4}$alkylamino: dimethylamino, diethylamino;
for $C_{1-4}$alkenyl: vinyl and allyl;
for $C_{2-4}$alkynyl: ethynyl and prop-2-ynyl;
for $C_{2-4}$alkenyloxy: vinyloxy and allyloxy;
for $C_{2-4}$alkynyloxy: ethynyloxy and prop-2-ynyloxy;
for $C_{1-4}$alkylthio: methylthio, ethylthio and propylthio;
for $C_{1-4}$alkylsulphinyl: methylsulphinyl, ethylsulphinyl and propylsulphinyl;
for $C_{1-4}$alkylsulphonyl: methylsulphonyl, ethylsulphonyl and propylsulphonyl;
for $C_{2-4}$alkanoylamino: acetamido, propionamido and butyramido;

A preferred class of compounds of the present invention is that wherein:

A is pyridyl, pyrimidinyl or pyridazinyl;
B is para-phenylene;
$X^1$ is CO, $SO_2$ or $CH_2$, preferably CO;
$T^1$ and $T^2$ are both N;
$L^1$ is ethylene or propylene;
$R^2$ and $R^3$ are joined to form an ethylene or propylene or methylenecarbonyl group; wherein the heterocyclic ring formed by $T^1$, $T^2$, $L^1$, $R^2$ and $R^3$ is unsubstituted or is substituted;
$X^2$ is $SO_2$;
Q is styryl optionally subsitituted (preferably 4-substituted), naphthyl optionally substituted (preferably 6-substituted) or is phenyl optionally substituted (preferably 4-substituted) by fluoro, chloro or bromo;
and pharmaceutically-acceptable salts thereof.

Particular compounds of the invention include:
1-(6-bromonaphth-2-ylsulphonyl)-4-[4-(4-pyridyl)benzoyl]piperazine;
1-(6-bromonaphth-2-ylsulphonyl)4-[4-(2-pyridyl)benzoyl]piperazine;
1-(6-bromonaphth-2-ylsulphonyl)4-[4-(4-pyrimidinyl)benzoyl]piperazine;
1-(6-chloronaphth-2-ylsulphonyl)4-[4-(4-pyridyl)benzoyl]piperazine;

1-(6-chloronaphth-2-ylsulphonyl)-3-methoxycarbonyl-4-[4-(4-pyrimidinyl)benzoyl]piperazine;
1-(6-bromonaphth-2-ylsulphonyl)4-[4-(2-methylpyrimidin-4-yl)benzoylpiperazine;
1-(6-bromnonaphth-2-ylsulphonyl)4-[4-(2,6-dimethylpyrimidin-4-yl)benzoyl]piperazine;
1 (6-chloronaphth-2-ylsulphonyl)-4-[4-(4-pyrimidinylabenzoyl]piperazine;
1-(6-bromonaphth-2-ylsulphonyl)-4-[4-(3-fluoro-4-pyridyl)benzoyl]piperazine;
1-(6-bromonaphth-2-ylsulphonyl)-3-hydroxymethyl-4-[4-(4-pyridyl)benzoyl]piperazine,
1-(6-bromonaphth-2-ylsulphonyl)-3-ethoxycarbonyl-4-[4-(4-pyridyl)benzoyl]piperazine;
1-(6-bromonaphth-2-ylsulphonyl)-4-[2-methoxycarbonyl-4-(4-pyridylabenzoyl]piperazine;
1-(6-bromonaphth-2-ylsulphonyl)-4-[4-(4-pyridazinyl)benzoyl]piperazine;
1-(6-bromonaphth-2-ylsulphonyl)-4-[4-(2-methyl-4-pyridyl)benzoyl]piperazine;
1-(4-chloro-$\underline{E}$-styrylsulphonyl)-4-[4-(4-pyridyl)benzoyl]piperazine;
1-(6-bromonaphth-2-ylsulphonyl)4-[4-(3-pyridazinyl)benzoyl]piperazine;
1-(6-bromonaphth-2-ylsulphonyl)3-oxo-4-[4-(4-pyrimidinyl)benlzoyl]piperazine;
1-(6-bromonaphth-2-ylsulphonyl)-4-[4-(2-cyano-4-pyridyl)benzoyl]piperazine;
1-(6-bromonaphth-2-ylsulphonyl)4-[2-methoxy-4-(4-pyridazinyl)benzoyl]piperazine;
1-(6-bromonaphth-2-ylsulphonyl)-4-[4-(1,2,3-thiadiazol-4-yl)benzoyl]piperazine;
1-(6-bromonaphth-2-ylsulphonyl)-4-[4-(4-pyridyl)benzoyl]homopiperazine;
1-(6-bromonaphth-2-ylsulphonyl)4-[4-(3,5-diamino-1,2,4-triazol-1-yl)benzoyl]piperazine;
1-(6-bromonaphth-2-ylsulphonyl)-3-(4-thiomorpholinocarbonyl)-4-[4-(4-pyrimidinyl)benzoyl]piperazine;
1-(6-bromonaphth-2-ylsulphonyl)-4-[4-(3-furanyl)benzoyl]piperazine; and
1-(6-methoxynaphth-2-ylsulphonyl)4-[4-(4-pyridyl)benzoyl]piperazine.

Particularly preferred compounds of the invention are;

1-(6-bromonaphth-2-ylsulphonyl)4-[4-(4-pyrimidinyl)benzoyl]piperazine;
1-(6-chloronaphthyl-2-ylsulphonyl)-4-[4-(4-pyridylabenzoyl]piperazine; and
1-(6-bromonaphth-2-ylsulphonyl)4-[4-(4-pyradazinyl)benzoyl]piperazine.

A heterocyclic derivative of the formula I, or pharmaceutically-acceptable salt thereof, may be prepared by any process known to be applicable to the preparation of related compounds. Such procedures are provided as a further feature of the invention and are illustrated by the following representative processes in which, unless otherwise stated A, B, $X^1$, $T^1$, $T^2$, $L^1$, $R^2$, $R^3$, $X^2$ and Q have any of the meanings defined hereinbefore wherein any functional group, for example amino, alkylamino, carboxy or hydroxy, is optionally protected by a protecting group which may be removed when necessary.

Necessary starting materials may be obtained by standard procedures of organic chemistry.

According to another aspect, the present invention provides a process for preparing a compound of formula (I) or a pharmaceutically acceptable salt thereof, which comprises:

(a) For the production of those compounds of the formula (I) wherein $T^1$ is N and $X^1$ is CO, the reaction, conveniently in the presence of a suitable base, of an amine of formula (II)

$$HN(R^2)-L^1-T^2(R^3)-X^2Q \qquad (II)$$

with an acid of the formula (III)

$$A-B-COOH \qquad (III)$$

or a reactive derivative thereof.

A suitable reactive derivative of an acid of the formula (III) is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated amide such as 1,1'-carbonyldiimidazole; an active ester, for example an ester formed by the reaction of the acid and a phenol such as pentafluorophenol, an ester such as pentafluorophenyl trifluoroacetate or an alcohol such as $\underline{N}$-hydroxybenzotriazole or $\underline{N}$-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as $\underline{N,N}$'-dicyclohexylcarbodiimide or $\underline{N}$-(3-dimethylaminopropyl)-$\underline{N}$'-ethyl-carbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, $\underline{N,N}$-dimethylformamide, $\underline{N,N}$-dimethylacetamide, $\underline{N}$-methylpyrrolidin-2-one, dimethylsulphoxide or acetone, and at a temperature in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. An arylmethyl group such as a benzyl group may be removed for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) For the production of those compounds of the formula (I) wherein $T^1$ is CH and $X^1$ is O by the reaction, conveniently in the presence of a suitable coupling agent, of a compound of the formula (IV):

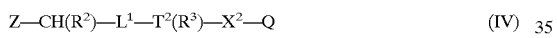

Z—CH($R^2$)—$L^1$—$T^2$($R^3$)—$X^2$—Q                     (IV)

wherein Z is a displaceable group, with a phenolic compound of the formula (V):

A—B—OH                     (V)

A suitable value for the displaceable group Z is, for example, a halo or sulphonyloxy group, for example a fluoro, chloro, bromo, mesyloxy or 4-tolylsulphonyloxy group.

A suitable reagent for the coupling reaction when Z is a halo or sulphonyloxy group is, for example, a suitable base, for example, an alkali or alkaline earth metal carbonate, hydroxide or hydride, for example sodium carbonate, hydroxide or hydride, for example sodium carbonate, potassium carbonate, sodium hydroxide, potassium hydroxide, sodium hydride or potassium hydride. The alkylation reaction is preferably performed in a suitable inert solvent or diluent, for example N,-dimethylformamide. N,N-dimethylacetamide, dimethylsulphoxide, acetone, 1,2-dimethoxyethane or tetrahydrofuran, and at a temperature in the range, for example, −10° to 150° C., conveniently at or near ambient temperature. An analogous procedure may be employed for the preparation of those compounds of the formula (I) wherein $T^1$ is CH and $X^1$ is S.

A suitable reagent for the coupling reaction of the alcohol of the formula (IV) wherein Z is a hydroxy group, where the hydroxy group is converted in situ to a displaceable group as defined above, is, for example, the reagent obtained when said alcohol is reacted with a di-$C_{1-4}$alkyl azodicarboxylate in the presence of a triarylphosphine or tri-$C_{1-4}$alkylphosphine, for example with diethyl azodicarboxylate in the presence of triphenylphosphine or tributylphosphine.

The reaction is preferably performed in a suitable inert solvent or diluent, for example acetone, 1,2-dimethoxyethane or tetrahydrofuran, and at a temperature in the range, for example, 10 to 80° C., conveniently at or near ambient temperature.

(c) For the production of those compounds of the formula (I) wherein $T^1$ is N and $X^1$ is CH($R^4$), the reductive amination of a keto compound of the formula (VI):

A—B—CO—$R^4$                     (VI)

wherein $R^4$ is hydrogen or $C_{1-4}$ alkyl, with an amine of the formula (II) as defined above.

Any reducing agent known in the art for promoting a reductive amination reaction may be employed. A suitable reducing agent is, for example, a hydride reducing agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride. The reaction is performed at a temperature in the range, for example, 10° to 80° C., conveniently at or near ambient temperature.

(d) The reaction of a compound of the formula (VII):

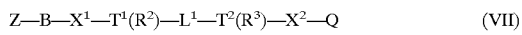

Z—B—$X^1$—$T^1$($R^2$)—$L^1$—$T^2$($R^3$)—$X^2$—Q                     (VII)

wherein Z is a displaceable group such as halo, with an activated derivative of ring A. Suitable activated derivatives include metalised derivatives, such as with zinc or tin and borane derivatives. The activated derivative of ring A is reacted with a compound of the formula (VII) to effect cross coupling where Z is triflate or a halo group, such as iodo, bromo or chloro. Suitably the reaction is catalysed by use of a transition state metal catalyst, such as palladium, for example tetrakis (triphenylphosphine) palladium (0).

Alternatively it is possible that ring A contains the displaceable group Z and ring B is activated, and the reaction performed as described above.

Compounds of the formula (VII) not suitable for this method are those which contain a halo substituent on B, Q or $L^1$.

(e) By forming A ring on compounds of formula (VII), wherein Z is a functional group capable of cyclisation. Suitable reagents and conditions are described below in preparing compounds of formula (III) by cyclisation.

(f) For the production of compounds wherein $T^2$ is N, the reaction of a compound of the formula (VIII):

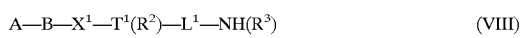

A—B—$X^1$—$T^1$($R^2$)—$L^1$—NH($R^3$)                     (VIII)

with a compound of the formula (IX):

Z—$X^2$—Q                     (IX)

wherein Z is a displaceable group for example chloro, under conditions similar to those of process (a) above.

(g) For the production of compounds wherein $T^1$ is N and $X^1$ is SO or $SO_2$, the reaction of a compound of the formula (II) as defined above with a compound of the formula (X):

A—B—$SO_x$—Z (X)

wherein x is one or two and Z is a displaceable group: under appropriate conventional coupling conditions, similar to those of process variant (a) above.

(h) For production of compounds of the formula (I) by coupling $T^2$ to Q and thus preparing the —$T^2$—$X^2$—Q moiety, methods analogous to those described in process variants (a), (c) and (g) for preparing the B—$X^1$—$T^1$— moiety may be employed.

(i) For the production of compounds of the formula (I) wherein $X^1$ is a group of the formula SO, $SO_2$, wherein B bears a $C_{1-4}$alkylsulphinyl, $C_{1-4}$alkylsulphonyl, 1-oxothiomorpholino or 1,1-dioxothiomorpholino group, wherein $X^2$ is a group of the formula SO or $SO_2$, wherein Q bears a $C_{1-4}$alkylsulphinyl, $C_{1-4}$alkylsulphonyl, phenylsulphinyl, phenylsulphonyl, heteroarylsulphinyl or heteroarylsulphonyl group, the oxidation of the corresponding compound of the formula (I) which contains $X^1$ as a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15 to 35° C. Suitable reagents and conditions are described in, for example. Page G. O.; Synth. Commun. 23, (1993) 6, 765–769. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound. Those compounds of the formula (I) which contain oxygen labile groups (such as A ring is pyridyl) are probably not suitable intermediates for this process step, unless oxidation of such groups is desired.

Compounds of formula (II) wherein $T^2$ is N may be prepared by the reaction of a compound of the formula (XI)

P—N—($R^2$)—$L^1$—NH($R^3$) (XI)

, wherein P is a protecting group, with a compound of formula (IX), as defined above, in an analogous manner as described above in method (f) above, and subsequently removing the protecting group. In addition compounds of formula (II) may be prepared in an analogous manner as described above in methods (h) and (i).

Compounds of formula (IV) may be prepared in an analogous manner as described for the preparation of compounds of formula (II).

Compounds of formula (III) may be prepared by the coupling of a compound of formula (XII), wherein Z is a displaceable group, preferably halo,

Z—B—COOH (XII)

with an activated derivative of ring A as described, for example, in method (d) above. Ideally the reaction is catalysed with a palladium catalyst as described in Example 1 (c) and Example 3 (a) below. Suitable reagents and conditions are described in Martin A. R.; Acta. Chem. Scand., 47, 221–230, (1993); Mitchell T. N.; Synthesis, 803, (1992) and Stille, J. K., Angew. Chem. Int. Ed. Engl. 25, 508–524, (1986).

Suitable non-catalysed coupling reactions include those described in Shiao, M-J. et. al., Synlett., 655, (1992).

Synthesis of stannane intermediates which may be required for palladium catalysed reactions are described in Hylarides, M. D. et. al., Journal of Organometallic Chemistry, 367, 259–265, (1989).

Alternatively compounds of formula (III) may be prepared by forming A rings on compounds of formula (XII), wherein Z is a functional group capable of cyclisation, by cyclisation reaction. Suitable reagents and conditions are described in Bredereck H. Chem. Ber.; 96, 1505, (1963); Fuchigami. T., Bull. Chem. Soc. Jpn., 49, p3607, (1976); Huffman K. R., J. Org. Chem. 28, p1812, (1963), Palusso, G., Gazz. Chim. Ital., 90, p1290, (1960) and Ainsworth C. J., Heterocycl. Chem., 3, p470, (1966). Such reactions are particularly suited to the formation of 5-membered A rings. Processes suitable for synthesis of starting materials in such cyclisation reactions are described, for example, in Zhang M. Q. et. al; J. Heterocyclic. Chem.; 28, 673, (1991) and Kosugi, M. et al., Bull. Chem. Soc. Jpn., 60, 767–768 (1987).

Compounds of formula (V), (VI) and (X) may be prepared in an analogous manner as described for preparing compounds of formula (III).

Compounds of formula (VII) wherein $T^2$ is N may be prepared by the reaction of a compound of the formula (XIII)

B—$X^1$—$T^1$($R^2$)—$L^1$—NH($R^3$) (XIII)

with a compound of formula (IX), as defined above, in an analogous manner as described above in method (f).

Compounds of formula (XIII) may be prepared by the reaction of a compound of the formula (XIV)

Z—$T^1$($R^2$)—$L^1$—N($R^3$)P (XIV)

wherein Z is a displaceable group or hydrogen and P is a protecting group in an analogous manner is described in method (a), (b) and (c) above and subsequently effecting removal of the protecting group.

Compounds of formula (VIII) may be prepared by the reaction of a compound of formula (XV)

Z—$T^1$($R^2$)—$L^1$—N($R^3$)P (XV)

wherein Z is a displaceable group or hydrogen and P is a protecting group, in an analogous method as described in method (a),(b) and (c) above and subsequently effecting removal of the protecting group.

Compounds of formula (IX), where $X^2$ is SO or $SO_2$, may be prepared by oxidation of compound of formula (IX), where $X^2$ is S, in an analogous method as described in method (h) above. Suitable reagents and conditions are described in Newman, M. S., et. al. Organic Synthesis. Vol. 51, p139. Methods for preparation of the thio analogues of Q are described in Kharasch, N. et. al., J. Am. Chem. Soc., 73, p3240, 1951.

When a pharmaceutically-acceptable salt of a compound of the formula (I) is required, it may be obtained, for example, by reaction of said compound with a suitable acid or base using a conventional procedure.

When an optically active form of a compound of the formula (I) is required, it may be obtained, for example, by carrying out one of the aforesaid procedures using an optically active starting material or by resolution of a racemic form of said compound using a conventional procedure, for example by the formation of diastereomeric salts, use of chromatographic techniques, conversion using chirally specific enzmatic processes, or by additon of temporary extra chiral groupd to aid separation.

As stated previously, the compounds of the formula (I) are inhibitors of the enzyme Factor Xa. The effects of this inhibition may be demonstrated using one or more of the standard procedures set out hereinafter a) Measurement of Factor Xa Inhibition An in vitro assay system based on the method of Kettner et al., *J. Biol. Chem.*, 1990, 265, 18289–18297, whereby various concentrations of a test compound are dissolved in a pH 7.5 buffer containing 0.5% of a polyethylene glycol (PEG 6000) and incubated at 37° C. with human Factor Xa (0.001 Units/ml, 0.3 ml) for 15 minutes. The chromogenic substrate S-2765 (KabiVitrum AB, 20 $\mu$M) is added and the mixture is incubated at 37° C. for 20 minutes whilst the absorbance at 405 nm is measured. The maximum reaction velocity (Vmax) is determined and compared with that of a control sample containing no test compound. Inhibitor potency is expressed as an $IC_{50}$ value.

b) Measurement of Thrombin Inhibition

The procedure of method a) is repeated except that human thrombin (0.005 Units/ml) and the chromogenic substrate S-2238 (KabiVitrum AB. 7 $\mu$M) are employed.

c) Measurement of Anticoagulant Activity

An in vitro assay whereby human, rat or rabbit venous blood is collected and added directly to a sodium citrate solution (3.2 g/100 ml, 9 parts blood to 1 part citrate solution). Blood plasma is prepared by centrifugation (1000 g, 15 minutes) and stored at 2–4° C. Conventional prothrombin time (PT) tests are carried out in the presence of various concentrations of a test compound and the concentration of test compound required to double the clotting time, hereinafter referred to as CT2, is determined. In the PT test, the test compound and blood plasma are incubated at 37° C. for 10 minutes. Tissue thromboplastin with calcium (Sigma Limited, Poole England) is added and fibrin formation and the time required for a clot to form are determined.

d) Rat Disseminated Intravascular Coagulation in vivo Activity Test:

Fasted male Alderley Park rats (300–450 g) are pre-dosed by oral gavage (5 mls/kg) with compound or vehicle (5% DMSO/PEG200) at various times before being anaesthetised with Intraval® (120 mg/kg i.p.). The left jugular vein and the right carotid artery are exposed and cannulated. A 1 mL blood sample is taken from the carotid canular into 3.2% trisodium citrate. 0.5 mL of the whole blood is then treated with EDTA and used for platelet count determination whilst the remainder is centrifuged (5 mins, 20000 g) and the resultant plasma frozen for subsequent drug level, fibrinogen or thrombin antithrombin (TAT) complex determinations. Recombinant human tissue factor (Dade Innovin Cat.B4212-50), reconstituted to the manufacturers specification, is infused (2 mL/kg/hr) into the venous canular for 60 minutes. Immediately after the infusion is stopped a 2 mL blood sample is taken and platelet count, drug level, plasma fibrinogen concentration and TAT complex are determined as before. Platelet counting is performed using at Coulter T540 blood analyser. Plasma fibrinogen and TAT levels are dertermining using a clotting assay (Sigma Cat.880-B) and TAT ELISA (Behring) respectively. The plasma concentration of the compound is bioassayed using human Factor Xa and a chromogenic substrate S2765 (Kabi), extrapolated from a standard curve (Fragmin) and expressed in Anti-Factor Xa units. The data is analysed as follows; tissue factor-induced reductions in platelet count are normalised with respect to pre-dose platelet count and drug activity expressed as a percent inhibition of tissue factor-induced thrombocytopenia when compared to vehicle treated animals. Compounds are active if there is statistically significant (p<0.05) inhibition of TF-induced thrombocytopenia.

e) An ex vivo Assay of Anticoagulant Activity

The test compound is administered intravenously or orally to a group of Alderley Park Wistar rats. At various times thereafter animals are anaesthetised, blood is collected and PT coagulation assays analogous to those described hereinbefore are conducted.

f) An in vivo Measurement of Antithrombotic Activity

Thrombus formation is induced using an analogous method to that described by Vogel et al., *Thromb. Research*, 1989, 54, 399–410. A group of Alderley Park Wistar rats is anaesthetised and surgery is performed to expose the vena cava. Collateral veins are ligated and two loose sutures are located, 0.7 cm apart, round the inferior vena cava. Test compound is administered intravenously or orally. At an appropriate time thereafter tissue thromboplastin (30 $\mu$l/kg) is administered via the jugular vein and, after 10 seconds, the two sutures are tightened to induce stasis within the ligated portion of vena cava. After 10 minutes the ligated tissue is excised and the thrombus therein is isolated, blotted and weighed.

In general compounds of the formula I possess activity at the following concentrations or doses in at least one of the above tests a) to c):

test a): $IC_{50}$ (Factor Xa) in the range, for example, 0.001–25 $\mu$M;

test b): $IC_{50}$ (thrombin), for example, greater than 40 $\mu$M;

test c): CT2 (PT) in the range, for example, 0.1–50 $\mu$M.

A feature of the invention is a compound of formula (I), or a pharmaceutically acceptable salt thereof, for use in medical therapy.

According to a further feature of the invention there is provided a pharmaceutical composition which comprises a heterocyclic derivative of the formula (I), or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocyclic derivative of the formula (I), or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclic derivative of formula (I), or a pharmaceutically-acceptable salt thereof, for use in a method of treatment of the human or animal body by therapy.

The invention also includes the use of such an active ingredient in the production of a medicament for use in:
(i) producing a Factor Xa inhibitory effect;
(ii) producing an anticoagulant effect;
(iii) producing an antithrombotic effect;
(iv) treating a Factor Xa mediated disease or medical condition;
(v) treating a thrombosis mediated disease or medical condition;
(vi) treating coagulation disorders; and/or
(vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formula (I) will naturally vary according to the nature and severity of the medical condition, the age and sex of the animal or patient being treated and the route of administration, according to well known principles of medicine. As mentioned above, compounds of the formula (I) are useful in the treatment or prevention of a variety of medical disorders where anticoagulant therapy is indicated. In using a compound of the formula (I) for such a purpose, it will generally be administered so that a daily oral dose in the range, for example, 0.5 to 100 mg/kg body weight/day is received, given if required in divided doses. In general lower doses will be administered when a parenteral route is employed, for example a dose for intravenous administration in the range, for example, 0.01 to 10 mg/kg body weight/day will generally be used. For preferred and especially preferred compounds of the invention, in general, lower doses will be employed, for example a daily dose in the range, for example, 0.1 to 10 mg/kg body weight/day. In general a preferred dose range for either oral or parenteral administration would be 0.01 to 10 mg/kg body weight/day.

Although the compounds of formula (I) are primarily of value as therapeutic or prophylactic agents for use in warm-blooded animals including man, they are also useful whenever it is required to produce an anticoagulant effect, for example during the ex-vivo storage of whole blood or in the development of biological tests for compounds having anticoagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known antihypertensive agent.

The invention will now be illustrated in the following Examples in which, unless otherwise stated:

(i) evaporations were carried out by rotary evaporation in vacuo and work-up procedures were carried out after removal of residual solids by filtration;

(ii) operations were carried out at room temperature that is in the range 18–25° C. and under an atmosphere of an inert gas such as argon;

(iii) column chromatography (by the flash procedure) and medium pressure liquid chromatography (MPLC) were generally performed on Merck Kieselgel silica (Art. 9385) or Merck Lichroprep RP-18 (Art. 9303) reversed-phase silica obtained from E. Merck, Darmstadt, Germany: alternatively high pressure liquid chromatography (HPLC) was performed on a Dynamax C-18 60 Å preparative reversed-phase column;

(iv) yields are given for illustration only and are not necessarily the maximum attainable;

(v) the end-products of the formula (I) have satisfactory microanalyses and their structures were confirmed by nuclear magnetic resonance (NMR) and mass spectral techniques; unless otherwise stated, $CD_3SOCD_3$ solutions of the end-products of the formula I were used for the determination of NMR spectral data, chemical shift values were measured on the delta scale; the following abbreviations have been used: s, singlet; d, doublet; t, triplet, q, quartet; m multiplet;

(vi) intermediates were not generally fully characterised and purity was assessed by thin layer chromatographic, infra-red (IR) or NMR analysis;

(vii) melting points were determined using a Mettler SP62 automatic melting point apparatus or an oil-bath apparatus; melting points for the end-products of the formula I were generally determined after crystallisation from a conventional organic solvent such as ethanol, methanol, acetone, ether or hexane, alone or in admixture; and (viii) the following abbreviations have been used:

| | |
|---|---|
| DMF | N,N-dimethylformamide: |
| EtOAc | ethyl acetate; |
| DMSO | dimethylsulphoxide. |

Example 1

Methyl 4-(4-pyrimidinyl)benzoate (0.41 g, 1.9 mmol) was stirred at room temperature in ethanol (20 mL) and 2N $NaOH_{(aq)}$ (20 mL) for 1 hour. 2N $HCl_{(aq)}$ was added until a precipitate formed. The resulting suspension was concentrated in vacuo and azeotroped with toluene. Thionyl chloride (100 mL) and DMF (1 drop) were added and the reaction mixture refluxed for 1 hour. The reaction mixture was concentrated in vacuo and azeotroped twice with dichloromethane to yield 4-(4-pyrimidinyl)benzoyl chloride. The acid chloride was suspended in dichloromethane (100 mL) and 1-(6-bromonaphth-2-ylsulphonyl)piperazine hydrochloride (0.545 g, 1.5 mmol) added as a solid in two portions followed by triethylamine (2.2 mL, 15 mmol). The reaction mixture was stirred overnight at room temperature then concentrated in vacuo. The resulting solid was separated between ethyl acetate (100 mL) and water (2×100 mL). The organic layer was dried over magnesium sulphate, filtered and concentrated in vacuo to yield a black oil which was subjected to chromatography (SiO$_2$: 40%, 50%, 60% Ethyl acetate/Hexane) to yield 1(6-bromonaphth-2-ylsulphonyl)4-[4-(4-pyrimidinyl)benzoyl]piperazine as a white solid; 1H NMR (250 MHz, DMSO-d$_6$) δ=2.94 to 3.18 ppm (m,4H), δ=3.40 to 3.83 ppm (m,4H), δ=7.49 ppm (d,2H), δ=7.83 ppm (m,2H), δ=8.10 ppm (dd,1H), δ=8.14 to 8.23 ppm (m,4H), δ=8.43 ppm (d,1H), δ=8.49 ppm (s,1H), δ=8.89 ppm (d,1H), δ=9.26 ppm (s,1H); MS (M+H)$^+$ 536.

Methyl 4-(4-pyrimidinyl)benzoate was prepared as follows:

(a) 4(3H)-Pyrimidone (7.00 g, 72.8 mmol) was refluxed in thionyl chloride (50 mL) and DMF (3 mL) for 1 hour. A clear solution was not obtained so a further portion of thionyl chloride (50 ml) was added and the reaction mixture refluxed for a further hour. The reaction mixture was concentrated in vacuo. Ether (500 ml) was added and the solid "scratched". The resulting yellow solid was filtered off and washed with ether. A precipitate formed in the filtrate. This was filtered off to yield 4-chloropyrimidine as a pale brown solid (4.97 g); 1H NMR (250 MHz DMSO-d$_6$) δ=6.62 ppm (d,1H), δ=8.07 ppm (dd,1H) δ=9.11 ppm (s,1H); MS (M+H)$^-$ 115.

(b) 4-Carboxybenzene boronic acid (10.22 g, 61.2 mmol) was refluxed overnight in methanol (70 mL) with concentrated sulphuric acid (0.5 mL). The reaction mixture was allowed to cool to room temperature then concentrated in vacuo. The resulting oil was separated between ethyl acetate (200 mL) and water (200 mL). The organic layer was dried over magnesium sulphate, filtered and concentrated in vacuo to yield the corresponding methyl ester as a white solid (9.85 g); $^1$H NMR (250 MHz, DMSO-d$_6$) δ=3.85 ppm (s,3H), δ=7.89 ppm (s,4H), δ=8.19 ppm (s,2H); MS (M–H)$^-$ 179.

(c) 1,1'-Bis(diphenylphosphino)ferrocene (2.48 g, 4.5 mmol) and palladium (II) acetate (1.0 g, 4.5 mmol) were stirred at 50° C. in toluene (25 mL) under an atmosphere of nitrogen for 30 minutes, then allowed to cool to room temperature. The boronic acid methyl ester from b) above (2.2 g, 11.2 mmol), 4-chloropyrimidine hydrochloride from a) above (1.69 g, 11.2 mmol) and potassium fluoride (3.9 g, 67 mmol) were added followed by water (25 mL). The reaction mixture was refluxed overnight under an atmosphere of nitrogen. The reaction mixture was separated between ethyl acetate (100 ml) and water (100 ml). The organic layer was dried over magnesium sulphate, filtered and concentrated in vacuo to yield a black oil which was subjected to chromatography (SiO2: 100% Ethyl acetate) to yield methyl 4-(4-pyrimidinyl)benzoate as a brown solid (1.17 g); 1H NMR (250 MHz DMSO-d$_6$) δ=3.91 ppm (s,3H), δ=8.13 & 8.36 ppm (dd,4H), δ=8.19 ppm (dd,1), δ=8.94 ppm (d,1H), δ=9.32 ppm (d,1H); MS (M+H)$^+$ 215.

Example 2

Methyl 4-(4-pyrimidinyl)benzoate (0.72 g, 3.4 mmol) was stirred at room temperature in ethanol (100 mL) and 2N NaOH$_{(aq)}$ (20 mL) for 1 hour. 2N HCl$_{(aq)}$ was added until a precipitate formed. The resulting suspension was concentrated in vacuo and azeotroped with toluene. Thionyl chloride (100 mL) and DMF (1 drop) were added and the reaction mixture refluxed for 1 hour. The reaction mixture was concentrated in vacuo and azeotroped with toluene to yield 4-(4-pyrimidinyl)benzoate. The acid chloride was suspended in dichloromethane (100 mL) and 4-(6-chloronaphth-2-ylsulphonyl)-2-methoxycarbonylpiperazine hydrochloride (1.0 g, 2.7 mmol) added as a solid in one portion followed by triethylamine (3.8 mL, 27 mmol). The reaction mixture was stirred overnight at room temperature then concentrated in vacuo. The resulting solid was separated between ethyl acetate (200 mL) and water (2×200 mL). The organic layer was dried over magnesium sulphate, filtered and concentrated in vacuo to yield a brown solid which was subjected to chromatography (SiO$_2$: 100% Ethyl acetate) to yield 1-(6-chloronaphth-2-ylsulphonyl)-3methoxycarbonyl-4-[4-(4-pyrimidinyl)benzoyl]piperazine as an off white solid. This solid was again subjected to chromatography (SiO$_2$: 30%, 40%, 60%, 65% Ethyl acetate/Hexane) to yield a white crystalline solid (1.051 g); 1H NMR (250 MHz. DMSO-d$_6$) δ=2.75 ppm (m,1H), δ=2.92 to 4.64 ppm & 5.35 ppm (m,9H), δ=7.52 ppm (d,2H), δ=7.73 ppm (dd,1H), δ=7.80 ppm (dd,1H) δ=8.10 ppm (d,1H), δ=8.14 to 8.31 ppm (m,5H), δ=8.51 ppm (d,1H,), δ=8.89 ppm (d,1H,), δ=8.89 ppm (d,1H), δ=9.26 ppm (s,1H); MS (M+H)$^+$ 551.

Example 3

4-(4-Pyridyl)benzoic acid (238 mg, 1.2 mmol) was suspended in DMF (5 mL) with triethylamine (0.17 mL, 1.2 mmol). The reaction mixture was stirred at room temperature for 15 minutes then cooled to 5° C. Carbonyldiimidazole (194 mg, 1.2 mmol) was added and the reaction mixture allowed to warm slowly to room temperature over one hour. 4-(6-Bromonaphth-2-ylsulphonyl)piperazine hydrochloride (470 mg, 1.2 mmol) was added as a solid in one portion and the reaction mixture stirred for 2 days at room temperature. The reaction mixture was diluted with ethyl acetate (50 mL) and washed twice with saturated aqueous sodium hydrogen carbonate solution (2×50 mL). The organic layer was dried over MgSO$_4$, filtered and concentrated in vacuo. The resulting solid was subjected to chromatography (SiO$_2$: 2%, 4%, 6%, 8%, 10% methanol/ethyl acetate) to yield 1-(6-bromonaphth-2-ylsulphonyl)4-[4-(4-pyridyl)benzoyl]piperazine as a white solid (90 mg), $^1$H NMR (DMSO-d$_6$) δ=3.07 ppm (s,4H), δ=3.59 ppm (s,4H), δ=7.27 & 7.46 ppm (dd,4H), δ=7.18 & 8.64 ppm (dd,4H), δ=7.34 ppm (m,2H), δ=8.17 ppm (dd,2H), δ=8.39 ppm (d,1H), δ=8.47 ppm (s,1H); MS (M+H)$^+$ 536.

4-(4-Pyridyl)benzoic acid was prepared as follows:

a) 4-Cyanophenylboronic acid (1.49 g, 10 mmol), 4-bromopyridine hydrochloride (1.97 g, 10 mmol), 10% palladium-on-carbon (322 mg) and anhydrous sodium carbonate (2.15 g, 20 mmol) were refluxed in a mixture of ethanol (12 mL) and water (3 mL), overnight under an atmosphere of argon. The reaction mixture was filtered through diatomaceous earth, then concentrated in vacuo. The resulting white solid was separated between ethyl acetate (3×100 mL) and water (100 mL). The combined organic layers were dried over MgSO$_4$, filtered and concentrated in vacuo. The resulting solid was subjected to chromatography (SiO$_2$; 50%, 60%, 70%, 80% ethyl acetate/iso-Hexane) to yield 4-(4-pyridyl)benzonitrile as a crystalline white solid (1.60 g), $^1$H NMR (DMSO-d$_6$) δ=7.77 ppm (dd,2H), δ=7.99 ppm (m,4H), δ=8.69 ppm (dd,2H); MS (M+H)$^+$ 181.

b) 4-(4-Pyridyl)benzonitrile (0.5 g, 2.8 mmol) was dissolved in concentrated sulphuric acid (10 mL) and heated at 110° C. overnight. The reaction was allowed to cool to room temperature then poured into ice/water. Sodium hydroxide pellets were added until a precipitate formed. This was filtered off to yield 4-(4-pyridyl)benzamide as a white solid (0.40 g), $^1$H NMR (DMSO-d$_6$) δ7.77 ppm (d,2H), δ=7.89 ppm (d,2H), δ=8.02 ppm (d,2H), δ=8.65 ppm (br s,2H); MS (M+H)$^+$ 199.

c) 4-(4-Pyridyl)benzamide (0.35 g, 1.8 mmol) was suspended in ethanol (5 mL). 10% $^w/_w$ aqueous sodium hydroxide solution was added and the reaction mixture refluxed for two hours then allowed to cool to room temperature. The reaction mixture was adjusted to pH 7 with concentrated sulphuric acid. A white precipitate formed which was isolated by filtration to give 4-(4-pyridyl)benzoic acid (238 mg).

Example 4

4-(2-Pyridyl)benzoic acid (199 mg, 1 mmol) was suspended in DMF (5 mL) and triethylamine (0.14 mL. 1 mmol) was added. The reaction mixture was stirred at room temperature for 15 minutes then cooled to 5° C. Carbonyl diimidazole (162 mg, 1 mmol) was added and the reaction mixture allowed to warm slowly to room temperature over one hour. 1-(6-Bromonaphth-2-ylsulphonyl)piperazine hydrochloride (393 mg, 1 mmol) was added as a solid in one portion and the reaction mixture was stirred overnight at room temperature then concentrated in vacuo. The crude product was dissolved in ethyl acetate (50 mL) and washed with aqueous sodium bicarbonate solution (2×50 mL). The organic layer was dried over MgSO$_4$, filtered and concentrated in vacuo. The resulting off white solid was subjected to chromatography (SiO$_2$; 100% EtOAc) to yield 1-(6-bromonaphth-2-ylsulphonyl)4-14-(2-pyridyl)benzoy] piperazine as a white solid (92 mg); $^1$H NMR (DMSO-d$_6$) δ=3.09 ppm (s,4H), δ=3.62 ppm (s,4H), δ=7.37 ppm (t,1H), δ=7.51 to 7.99 ppm (m,4H), =7.42 and 8.08 ppm (dd,4H), δ=8.17 ppm (dd,2H), δ=8.40 ppm (d,1H) δ=8.47 ppm (s,1H), δ=8.66 ppm (dd,1H); MS (M+H)$^+$ 536.

Example 5

1-(6-Chloronaphth-2-ylsulphonyl)-4-(4-iodobenzoyl) piperazine (920 mg, 1.7 mmol), diethyl 3-pyridylborane (250 mg, 1.7 mmol), tetrabutyl ammonium bromide (110 mg, 0.34 mmol), tetrakis(triphenylphosphine) palladium (0) (69 mg, 0.06 mmol) and potassium hydroxide (286 mg, 5.1 mmol) were refluxed in dry tetrahydrofuran (100 mL) for two hours under an atmosphere of nitrogen. The reaction mixture was allowed to cool to room temperature then concentrated in vacuo. The resulting solid was subjected to flash chromatography (SiO$_2$: 100% CH2Cl2, 50% EtOAc/Hexane, 100% EtOAc) to yield an oil. The oil was dissolved in EtOAc (100 mL) and washed with saturated sodium hydrogen carbonate solution (100 mL). The EtOAc layer was separated, dried over MgSO$_4$, filtered and concentrated in vacuo to yield an off white foam which was triturated with hexane. This solid was subjected to chromatography (SiO$_2$: 40%, 50% 60%, 70% EtOAc/Hexane) to yield 1-(6-chloronaphth-2-ylsulphonyl)-4-[4-(3-pyridyl)benzoyl] piperazine as a white solid (322.4 mg); $^1$H NMR (DMSO-d$_6$) δ=3.1 ppm (s,4H), δ=3.6 ppm (s,4H), δ=7.46 ppm (d,2H), δ=7.5 to 7.67 ppm (m,1H), δ=7.70 to 7.79 ppm (m,3H), δ=7.83 pmm (dd,1H), δ=8.09 ppm (dt,1H), δ=8.15 ppm to 8.31 ppm (m,3H), δ=8.50 ppm (s,1H), δ=8.60 ppm (dd,1H), δ=8.90 ppm (d,1H); MS (M+H)$^+$ 492.

1-(6-Chloronaphth-2-ylsulphonyl)-4-(4-iodobenzoyl) piperazine was prepared as follows:

1-(6-Chloronaphth-2-ylsulphonyl)piperazine (0.65 g, 2.1 mmol) was dissolved in dichloromethane (50 mL) and triethylamine (2.9 mL, 21 mmol) was added at room temperature. 4-Iodobenzoyl chloride (0.56 g, 2.1 mmol) was added as a solid in one portion and the reaction mixture stirred for one hour at room temperature. The reaction mixture was concentrated in vacuo, then separated between EtOAc (100 mL) and saturated sodium hydrogen carbonate solution (100 mL). The EtOAc layer was separated, dried over MgSO$_4$, filtered and concentrated in vacuo. The resulting white solid was subjected to chromatography (SiO$_2$: 50% EtOAc/Hexane) to yield 1-(6-chloronaphth-2-ylsulphonyl)-4-(4-iodobenzoyl)piperazine as a white solid (097 g); $^1$H NMR (DMSO-d$_6$) δ=3.05 ppm (s,4H), δ=3.53 ppm (s,4H), δ=7.11 ppm & 7.74 ppm (dd,4H), δ=7.65 to 7.84 ppm (m,2H), δ8.10 ppm to 8.28 ppm (m,3H), δ=8.47 ppm (s,1H); MS (M+H)$^+$ 540.

Example 6

4-(2-Methyl-4-(3-pyridyl)benzoyl)piperazine (0.41 g, 1.5 mmol) was dissolved in dichloromethane (50 mL) at room temperature. 6-Chloronaphthalenesulphonyl chloride (0.38 g, 1.5 mmol) and triethylamine (1 ml, 7.5 mmol) were added and the reaction mixture stirred overnight. The reaction mixture was concentrated in vacuo. The crude product was dissloved in EtOAc (100 mL) and washed with saturated sodium hydrogen carbonate solution (100 mL). The EtOAc layer was separated, dried over MgSO$_4$, filtered and concentrated in vacuo. The resulting solid was subjected to chromatography (SiO$_2$: 50%, 60% EtOAc/Hexane) to yield 1-(6-chloronaphth-2-ylsulphonyl)-4-[2-methyl-4-(3-pyridyl)benzoyl]piperazine as a white solid (508.4 mg); $^1$H NMR (DMSO-d$_6$) δ=2.15 ppm (s,3H), δ=2.94 to 3.25 ppm (m,6H), δ=3.78 ppm (m,2H), δ=7.23 ppm (d,1H), δ=7.44 to 7.62 ppm (m,3H), δ=7.70 ppm (dd,1H), δ=7.84 ppm (dd, 1H), δ=8.08 ppm (m,1H), pyridyl 5-H), δ=8.12 to 8.28 ppm (m,3H), δ=8.48 ppm (s,1H), δ=8.59 ppm (dd,1H), δ=8.88 ppm (d,1H); MS (M+H)$^+$ 506.

4-(2-Methyl-4-(3-pyridyl)benzoyl)piperazine was prepared as follows:

a) 4-Bromo-2-methylbenzoic acid (11.55 g, 53.7 mmol) was suspended in thionyl chloride (40 mL). One drop of DMF was added and the resulting mixture was stirred at 69° C. until gas evolution ceased. The reaction mixture was concentrated in vacuo and azeotroped twice with toluene. The resulting oil was dissolved in dichloromethane (100 mL) and cooled to 5° C. tert-Butyl-1-piperazine carboxylate (10.0 g. 53.7 mmol) was added portionwise over one hour followed by triethylamine (37.5 mL, 260 mmol). The reaction mixture was stirred overnight at room temperature then concentrated in vacuo. The crude product was dissolved in ethyl acetate (750 mL) and washed with aqueous 2N sodium hydroxide solution and then with brine. The organic layer was dried over MgSO$_4$, filtered and concentrated in vacuo to yield a brown oil. The product crystallised from EtOAc/Hexane to yield beige crystals (9.01 g); $^1$H NMR (DMSO-d$_6$) δ=1.40 ppm (s,9H), δ=2.20 ppm (s,3H), δ=3.10 ppm (m,2H), δ=3.26 ppm (m,2H), δ=3.41 ppm (m,2H), δ=3.62 ppm (s,2H), δ=7.15 ppm (d,1H), δ=7.44 ppm (dd,1H), δ=7.52 ppm (d,1H); MS (M+H)$^+$ 383.

b) The product from a) above (3.83 g, 10 mmol), diethyl 3-pyridylborane (1.47 g, 10 mmol), tetrabutyl ammonium bromide (065 g, 2 mmol), tetrakis(triphenylphosphine) palladium (0) (0.40 g, 0.35 mmol) and potassium hydroxide (1.68 g, 30 mmol) were refluxed in dry tetrahydrofuran (75 mL) for two hours under an atmosphere of nitrogen. The reaction mixture was allowed to cool to room temperature then separated between EtOAc (250 mL) and water (2×500 mL). The EtOAc layer was separated, dried over MgSO$_4$, filtered and concentrated in vacuo. The resulting oil was subjected to flash chromatography (SiO$_2$: 100% EtOAc) to yield t-butyl 4-[2- methyl-4-(3-pyridyl)benzoyl]piperazine carboxylate as a brown solid (1.78 g); $^1$H NMR (DMSO-d$_6$) δ=1.41 ppm (s,9H), δ=2.60 ppm (s,3H), δ=3.17 ppm (m,2H), δ=3.27 ppm (m,2H), δ=3.44 ppm (m,2H), δ=3.66 ppm (s,2H), δ=7.61 ppm (d,1H), δ=7.49 ppm (dd,1H), δ=7.59 ppm (dd,1H), δ=7.61 ppm (s,1H), δ=8.08 ppm (m,1H), δ=8.58 ppm (dd,1H), δ=8.90 ppm (d,1H); MS (M+H)$^+$ 382.

c) The product from b) above (1.66 g, 4.35 mmol) was dissolved in dichloromethane (50 mL) at room temperature. Trifluoroacetic acid (10 mL) and the reaction mixture stirred for one hour at room temperature. The reaction mixture was concentrated in vacuo, then separated between EtOAc and 2N sodium hydroxide solution. The EtOAc layer was separated, dried over MgSO$_4$, filtered and concentrated in vacuo to yield 4-[2-methyl-4-(3-pyridyl)benzoyl]piperazine as a colourless oil (410 g).

Example 7

A solution of 4-(4-pyridyl)benzoic acid (398 mg), hydroxybenztriazole (338 mg) and dicyclohexylcarbodiimide (453 mg) were stirred at ambient temperature for 1 hour then 1-(6-chloronaphth-2-ylsulphonyl)piperazine (621 mg) was added to the resultant white suspension and stirring continued at ambient temperature for a further 16 hours. The reaction mixture was filtered and the filtrate concentrated in vacuo to a foam which was partially purified by flash chromatography at 3 psi on silica (Merck ART 9385) eluting with 2.5% v/v methanol in dichloromethane plus 0.1% SG 0.88 ammonia solution. This gave a white foam (473 mg). A portion of this foam (110 mg) was purified by preparative HPLC on a Dynamax® C-18 60 Å column eluting with 0.1% trifluoroacetic acid in aqueous acetonitrile over a gradient of 30%–70% acetonitrile. The solution was freeze-dried to produce a white foam. There was thus obtained 1-(6-chloronaphth-2-ylsulphonyl)4-[4-(4-pyridyl)benzoyl]piperazine the title compound as a trifluoroacetate salt (83.5 mg); mp 175–176° C.; $^1$NMR (250 MHz, DMSO-d$_6$ at 373° K) δ=3.17 (t,4H), 3.47 (t,4H), 7.47 (d,2H), 7.62–7.86 (m,6H), 8.08–848 (m,3H), 8.43 (s,1H), 8.66 (d,2H) ppm; MS: m/z 492/494 (M+H)$^+$ (1 Cl pattern).

Example 8

4-(2-Methyl-4-pyridyl)benzoic acid (62 mg), 1-(6-bromonaphth-2-ylsulphonyl) piperazine (94 mg) and 1-(3-dimethylaminopropyl)-3-ethylcarbodiimide hydrochloride (61 mg) were dissolved in DMF (2.5 ml) and the resultant solution stirred at ambient temperature for 16 hours. Excess DMF was removed in vacuo, water (10 ml) was added and the precipitate that formed was filtered, washed thoroughly with cold water and dried over P$_2$O$_5$. The solid thus obtained was purified by flash chromatography at 3 psi on silica (Merck ART 9385) eluting with 2.5% v/v methanol in dichloromethane. There was thus obtained the 1-(6-bromonaphth-2-ylsulphonyl)-4-[4-(2-methyl-4-pyridyl) benzoyl]piperazine (99 mg); mp 204–205° C.; $^1$H NMR (300 MHz, DMSO-d$_6$) δ=2.48 (s,3H), 3.03 (s,4H), 3.57 (broad s, 4H), 7.46 (t,3H), 7.56 (s,1H), 7.77(d,2H), 7.83(d, 2H), 8.17(q,2H), 8.42 (s,1H), 8.48 (d,2H) ppm; MS: m/z 550/552 (M+H)$^+$ (1 Br pattern).

4-(2-Methyl-4-pyridyl) benzoic acid was prepared as follows:

(a) iso-Amyl nitrite (7.9 g) was slowly added to a solution of ethyl 4-aminobenzoate (4.95 g) in 2-picoline (100 ml) at ambient temperature. The resultant mixture was heated at 100° C. for 2 hours then excess 2-picoline was removed in vacuo to give a black oil. The mixture of isomers thus obtained was purified by flash chromatography at 3 psi on silica (Merck ART 9385) eluting with 25% v/v ethyl acetate in iso-hexane. There was thus obtained ethyl 4-(2-methyl-4-pyridyl)benzoate (0.2 g) as brown gum of sufficient purity to continue: $^1$H NMR (300 MHz, DMSO-d$_6$) δ=1.32 (t,3H), 2.53 (s,3H), 4.33 (q,2H), 7.52 (d,1H), 7.61 (s,1H), 7.92 (d,2H), 8.05 (d,2H), 8.52 (d,1H) ppm; MS: m/z 242 (M+H)$^+$.

(b) Ethyl 4-(2-methyl-4-pyridyl)benzoate (185 mg) was dissolved in methanol (7.5 ml) and 1.0M NaOH (3.75 ml) and heated at 60° C. for 3 hours. The resulting mixture was reduced to low volume then water (10 ml) added, the solution neutralised to pH 7 with 1.0M HCl, the resulting precipitate filtered and dried over P$_2$O$_5$ to give 4-(2-methyl-4-pyridyl)benzoic acid as a light brown solid (73 mg); mp 293-294° C.; $^1$H NMR (300 MHz, DMSO-d$_6$) δ=2.52 (s,3H), 7.53 (d,1H), 7.62 (s,1H), 7.89 (d,2H), 8.04 (d,2H), 8.52 (d,1H) ppm. MS: m/z 214 (M+H)$^+$.

Example 9

4-(4-Pyridazinyl)benzoic acid (300 mg), 1-(6-bromonaphth-2-ylsulphonyl) piperazine (484 mg) and 1-(3-dimethlyaminopropyl)-3-ethylcarbodiimide hydrochloride (317 mg) were dissolved in DMF (7.5 ml) and the resultant solution stirred at ambient temperature for 16 hours. Water (50 ml) was added and the precipitate that formed was filtered, washed thoroughly with cold water and dried over P$_2$O$_5$. There was thus obtained 1-(6-bromonaphth-2-ylsulphonyl)4-[4-(4-pyridazinyl)benzoyl]piperazine (535 mg); mp 128–130° C.; $^1$H NMR (300 MHz, DMSO-d$_6$ at 373° K) δ=3.12 (s,4H), 3.57 (s,4H), 7.48 (d,2H), 7.80 (m,2H), 7.89 (d,2H), 7.94 (m,1H), 8.14 (d,2H), 8.39 (s,1H), 8.46 (s,1H), 9.26 (d,1H), 9.58(s,1H) ppm; MS: m/z 537/539 (M+H)$^+$ (1 Br pattern).

4-(4-Pyridazinyl)benzoic acid was prepared as follows:

(a) A solution of sodium nitrite (1.44 g) in water (3.0 ml) was added slowly to a stirred solution of ethyl 4-aminobenzoate (3.3 g) in 48% fluoroboric acid (9.4 ml) at 0° C. After the final addition the mixture was stirred at 0° C. for a further 0.5 hours, then filtered and washed with cold fluoboric acid (5.0 ml), then with ethanol and finally with diethylether. The ethyl (4-diazonium tetrafluoroborate)benzoate (4.60 g) thus obtained was mixed dry with potassium acetate (3.40 g) and 18-crown-6 (0.23 g) then treated with pyridazine (25 ml) at ambient temperature. The mixture rapidly turned black with evolution of nitrogen gas. After stirring at ambient temperature for 16 hours the excess pyridazine was removed in vacuo and the black residue thus obtained dissolved in ethyl acetate (50 ml) and washed with water (50 ml). The organic layer was dried (MgSO$_4$) and reduced to a black residue. The mixture of isomers thus obtained was then purified by flash chromatography on Merck ART 9385 silica eluting with ethyl acetate to give ethyl 4-(4-pyridazinyl) benzoate (1.04 g); mp 110–112° C.; $^1$H NMR (300 MHz, CDCl$_3$) δ=1.42 (t,3H), 4.43 (q,2H), 7.68 (dxd,1H), 7.75 (d,2H), 8.22 (d,2H), 9.28, (d,1H), 9.50 (d,1H) ppm; MS: m/z 229 (M+H)$^+$.

(b) Ethyl 4-(4-pyridazinyl)benzoate (580 mg) was dissolved in methanol (12.5 ml) and 1.0 M NaOH (12.7 ml) and heated at 60° C. for 4 hours. The resulting mixture was reduced to low volume then water (25 ml) added, the solution neutralised to pH 7 with 1.0M HCl, the resulting precipitate filtered and dried over P$_2$O$_5$ to give 4-(4-pyridazinyl)benzoic acid as a light brown solid (503 mg);

mp>330° C.; ¹H NMR (300 MHz, DMSO-d₆) δ=8.05 (m,5H), 9.32 (d,1H), 9.67 (s,1H) ppm, MS: m/z 201 (M+H)⁺.

Example 10

6-Bromonaphth-2-ylsulphonyl chloride (470 mg) was added in one portion to a mixture of 1-[2-methoxycarbonyl-4-(4-pyridyl)benzoyl]piperazine (500 mg) and triethylamine (311 mg) in dichloromethane (5 ml) at ambient temperature. After 10 minutes the mixture was reduced in vacuo and the residue thus obtained purified by flash chromatography at 3 psi on silica (Merck ART 9385) eluting first with dichloromethane, then 1% and 2% v/v methanol in dichloromethane. There was thus obtained 1-(6-bromonaphth-2-ylsulphonyl)4-[2-methoxycarbonyl-4-(4-pyridyl)benzoyl]piperazine (866 mg) as a foam; ¹H NMR (250 MHz CDCl₃) δ=3.03 (t,2H), 3.27 (t,2H), 3.34 (t,2H), 3.56 (s,3H), 3.94 (broad s,2H), 7.32 (b,1H) 7.48 (dxd,2H), 7.70–7.82 (m,3H), 7.86 (d,1H), 7.92(d,1H), 8.13(d,1H), 8.24 (d,1H), 8.32(s, 1H), 8.71 (dxd,2H) ppm; MS: m/z 594/596 (M+H)⁺ (1 Br pattern).

1-[2-methoxycarbonyl-4-(4-pyridyl)benzoyl]piperazine was prepared as follows:

STRUCTURE 'C'

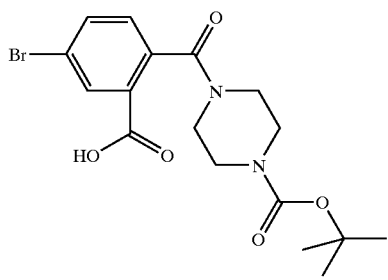

STRUCTURE 'D'

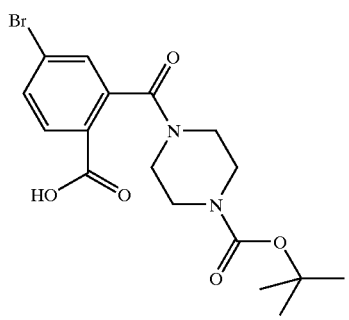

STRUCTURE 'E'

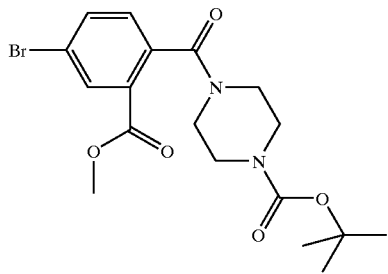

STRUCTURE 'F'

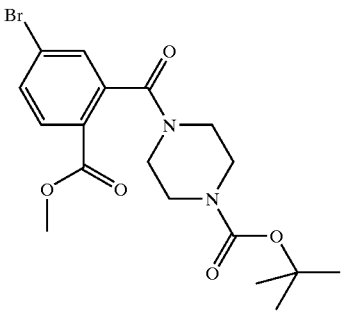

A solution of t-butyloxycarbonylpiperazine (14.4 g) in chloroform (20 ml) was added dropwise to a solution of 4-bromophthalic anhydride (17.5 g) in chloroform (50 ml) at ambient temperature. The reaction mixture was stirred at 60° C. for 1 hour then reduced in vacuo to an oil. A mixture of isomers (31.9 g) was obtained (structures 'C' and 'D').

Potassium carbonate (10.7 g) and dimethyl sulphate (9.71 g) were added to a solution of the isomeric mixture of acids (C+D) in acetone (60 ml) and the mixture stirred for 2 hours at ambient temperature. The solution containing the esters (E+F) was filtered and the filtrate reduced in vacuo to a gum (33.0 g) which was purified by preparative HPLC using PhaseSep NP Silica, 15–35 μm, 60 Å and eluting with 25%–50% v/v ethyl acetate in iso-hexane. There was thus obtained structure 'E' (12.86 g), the slower running isomer, mp 131–132° C.; ¹H NMR (400 MHz, CDCl₃) δ=1.46 (s,9H), 3.14 (t,2H), 3.36 (broad s, 2H), 3.56 (broad s, 2H), 3.77 (broad s,2H), 3.89 (s,3H), 7.16 (d,1H) 7.71 (dxd,1H), 8.17 (d,1H) ppm; MS: m/z 427/429 (M+H)⁺ (1 Br pattern).

A solution of structure 'E' (4.27 g) in dry DMF (40 ml) was deoxygenated by bubbling argon for 5 minutes then tetrakis-triphenylphosphine palladium(0) (1.15 g), bis-triphenylphosphine palladium dichloride (0.70 g) and silver (1)oxide (2.32 g) were added and the mixture stirred for 5 minutes at 100° C. then trimethyl-(4-pyridyl)-stannane (3.63 g) was added and heating at 100° C. continued for 15 minutes. The mixture was allowed to cool and stirred at ambient temperature for 20 hours then filtered through diatomaceous earth and reduced in vacuo to a black residue which was stirred with 1.0M potassium fluoride (20 ml) for 1 hour then extracted with ethyl acetate (3×25 ml). The extracts were dried (MgSO₄), filtered and reduced to a black oil which was partially purified by flash chromatography at 3 psi on silica (Merck ART 9385) eluting with 25% and 50% v/v ethyl acetate in iso-hexane, then 2% and 4% v/v methanol in dichloromethane. A final purification by BIOTAGE® P45 MPLC eluting with ethyl acetate at 10 psi gave compound 1-tert-butoxycarbonyl-4-[2-methoxycarbonyl-4-(4-pyridyl)benzoyl]piperazine (1.94 g); mp 144–146° C.; ¹H NMR (300 MHz, CDCl₃) δ=1.46 (s,9H), 3.20 (t,2H), 3.39 (m,2H) 3.60 (m,2H), 3.81 (m,2H), 3.93 (s,3H), 7.42 (d,1H), 7.52 (d,2H), 7.84 (dxd,1H), 8.3 (d,1H), 8.73 (d,2H) ppm; MS: m/z 370 (M+H)⁺.

A 2.2 molar solution of hydrogen chloride in diethyl ether (2.9 ml) was added to a solution of structure 'B' (1.05 g) in dichloromethane (10 ml) and the mixture stirred for 4 hours at ambient temperature. The supernatant liquors were decanted and the remaining gum was triturated with diethyl ether to give a white solid which was treated with saturated aqueous sodium bicarbonate then extracted with ethyl acetate (3×10 ml). The combined organic extracts were dried (MgSO$_4$), filtered and reduced to give structure 1-[2-methoxycarbonyl-4-(4-pyridyl)benzoyl]piperazine (500 mg) as a white foam; $^1$H NMR (250 MHz, DMSO-d$_6$) δ=2.45 (m,21H), 2.62 (m,2H), 2.90 (m,2H), 3.39 (m,2H), 368 (s,3H), 7.33 (d,1H), 7.62 (dxd,2H), 7.93 (dxd,1H), 8.10 (d,1H), 8.53 (dxd,2H) ppm; MS: m/z 326 (M+H)$^+$.

Example 11

A stirred suspension of 4-(4-pyridyl)benzoic acid (sodium salt) (190 mg, 0.86 mmol) in dichloromethane (10 ml) was treated with oxalyl chloride (0.2 ml, 2.3 mmol) and DMF (catalytic amount). After stirring for 2 hours, further oxalyl chloride 0.2 ml, 2.3 mmol) and DMF (catalytic amount) was added and the suspension stirred a further 4 hours. The solvent was removed in vacuo and the residue, after drying, was suspended in dichloromethane (20 ml) and treated with 2-(hydroxymethyl)-4-(6-bromonaphth-2-ylsulphonyl) piperazine (300 mg, 0.78 mmol) and triethylamine (0.36 ml, 2.5 mmol). After stirring at room temperature overnight the reaction mixture was diluted with dichloromethane (20 ml) and water (20 ml). A copious precipitate appeared which was filtered off, dried and recrystallised from ethyl acetate (10 ml) to yield 1-(6-bromonaphth-2-ylsulphonyl)-3-(hydroxymethyl)-4-[4-(4-pyridyl)benzoyl] piperazine as a colourless solid (250 mg); $^1$H NMR (300 MHz, DMSO-d$_6$) δ=3–4 ppm (broad, 9H), δ7.2 ppm (d, 2H), δ=7.7 ppm (d, 2H), δ=7.8 ppm (m, 4H), δ=8.2 ppm (t, 2H), δ8.4 ppm (s,1H), δ=8.45 ppm (s,1H), δ=8.6 ppm (d, 2H); signals due ethyl acetate (1 mol eq) were also present; MS: (M+H)$^+$ 566/568 (1 Br pattern); analysis; found: C, 56.8; H, 4.9; N, 6.3%; C$_{27}$H$_{24}$BrN$_3$SO$_4$. C$_4$H$_8$O$_2$ requires: C, 56.9; H, 4.9; H, 4.9; N, 6.4%.

3-(Hydroxymethyl)-4-(6-bromonaphth-2-ylsulphonyl) piperazine was prepared as follows:

3-(Hydroxymethyl)piperazine monoacetate (1.1 g, 6.25 mmol) and triethylamine (2.2 ml, 2.5 eq) were stirred at room temperature in dichloromethane (50 ml) and the suspension treated with 6-bromonaphth-2-ylsulphonyl chloride (2.0 g, 6.5 mmol). The mixture was stirred overnight and then diluted with further dichloromethane (50 ml); the solution was washed sequentially with water, saturated sodium hydrogen carbonate solution and brine. Drying (PS paper) and evaporation yielded a colourless foam (1 g). This was subjected to chromatography (SiO$_2$; dichloromethane:methanol 19:1 v/v) to yield 2-(hydroxymethyl) 4-(6-bromonaphth-2-ylsulphonyl)piperazine as a colourless foam (670 mg) which was used without further purification, $^1$H NMR (300 MHz, CDCl$_3$) δ=2.3 ppm (t, 1H), δ=2.5 ppm (dt, 1H), δ=2.9–3.1 ppm (m, 3H), δ=3.5 ppm (dd, 1H), δ=3.6 ppm (m, 3H), δ=7.6–8.0 pmm (m, 4H), δ=8.1 ppm (s, 1H), δ=8.3 ppm (s, 1H): MS (M+H)$^+$ 385/387 (1 Br pattern).

Example 12

A stirred suspension of 4-(4-pyridyl)benzoic acid (133 mg, 0.67 mmol) in dimethylformamide (5 ml) was treated sequentially with 1-hydroxybenzotriazole hydrate (108 mg, 0.8 mmol), 1-(3-dimethylaminopropyl)-3-ethylcarbodiimide hydrochloride (153 mg, 0.8 mmol) and 1-(5-chlorobenzofuran-2-ylsulphonyl) piperazine (201 mg, 0.67 mmol). After stirring overnight the solvent was removed in vacuo and the residue chromatographed (Merck Art 9385 silica, eluting with dichloromethane containing 2% v/v of methanol) to yield 1-(5-chlorobenzofuran-2-ylsulphonyl)-4-[4-(4-pyridyl)benzoyl]piperazine as a colourless solid (40 mg), $^1$H NMR (CDCl$_3$) δ=3.2–3.4 ppm (broad s, 4H), δ=3.6-4.0 ppm (broad s, 4H), δ=7.35 ppm (s, 1H), δ=7.5 ppm (m, 6H), δ=7.7 ppm (m, 3H), δ=8.7 ppm (d, 2H), MS (M+H)$^+$ 482/484.

1-(5-Chlorobenzofuran-2-ylsulfonyl) piperazine was prepared as follows:

A stirred solution of piperazine (1.15 g, 13.4 mmol) and triethylamine (4.7 ml, 46.5 mmol) in dichloromethane (30 ml) was cooled to ~5° C. and a solution of 5-chlorobenzofuran-2-sulphonyl chloride (1.69 g, 7.8 mmol) in dichloromethane (10 ml) was added. Stirring was continued for 15 mins, and the reaction mixture then allowed to warm to ambient temperature over 2 hrs with stirring. Water was added to the reaction mixture, and the organic layer separated; this was washed with water (twice), brine (once), then dried (MgSO$_4$), filtered and evaporated to give a yellow gum. This was chromatographed (Merck Art 9385 silica, eluting with dichloromethane containing increasing amounts of methanol, up to 10% v/v) to give a yellow solid; trituration with diethyl ether gave 5-chlorobenzofuran-2-ylsulphonyl piperazine as a colourless solid (1.11 g) which was used without further purification, $^1$H NMR (CDCl$_3$) δ=2.8–3.0 ppm (t, 4H), δ=3.2–3.4 ppm (t, 4H), δ=7.3 ppm (s, 1H), δ=7.45 ppm (dd, 2H), δ=7.7 ppm (s, 1H); MS (M+H)$^+$ 301/303.

The requisite 5-chlorobenzofuran-2-ylsulphonyl chloride starting material was prepared as described in European Patent Application 0 355 827 (Mochida, Hydantoin derivatives).

Example 13

Further examples are described in Table 1

TABLE 1

| No. | Compound | Method | MS:m/z | $^1$H NMR (MHz, solvent) |
|---|---|---|---|---|
| 1 | 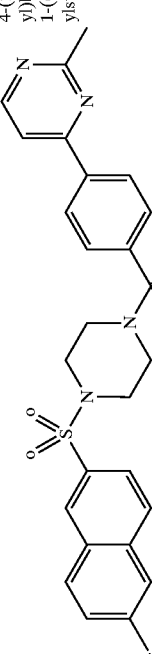 | 4-(2-methylpyrimidin-4-yl)benzoyl chloride¹ + 1-(6-bromonaphth-2-ylsulphonyl)piperazine | 551/553 (M + H)⁺ 1 Br pattern | (300MHz, DMSO-d₆)δ=2.66(s, 3H), 3.08 (brs, 4H), 3.53(brm, 4H), 7.46(d, 2H), 7.84 (m, 3H), 8.18(m, 4H), 8.40(s, 1H), 8.48 (s, 1H), 8.76(d, 1H)ppm. |
| 2 | 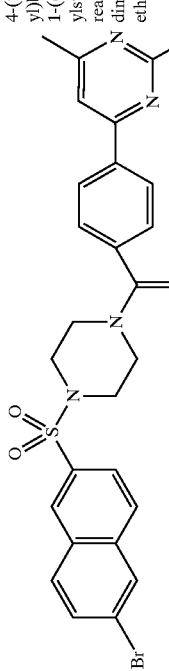 | 4-(2,6-dimethylpyrimidin-4-yl)benzoic acid² + 1-(6-bromonaphth-2-ylsulphonyl)piperazine: reaction using 1-(3-dimethylaminopropyl)-3-ethylcarbodiimide. | 565/567 (M + H)⁺ 1 Br pattern | (300MHz, DMSO-d₆)δ=2.46(s, 3H), 2.61 (s, 3H); 3.08(brm, 4H), 3.55(brm, 4H) 7.46 (d, 2H), 7.80(m, 3H), 8.16(m, 4H), 8.41(s, 1H), 8.46(s, 1H)ppm |
| 3 | 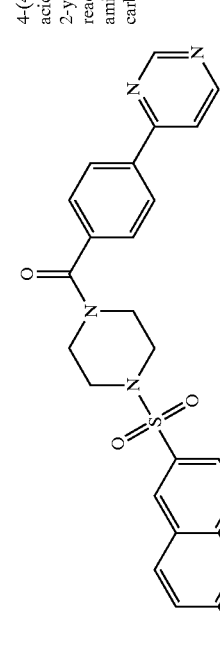 | 4-(4-pyrimidinyl)benzoic acid + 1-(6-chloronaphth-2-ylsulphonyl)piperazine: reaction using 1-(3-dimethylaminopropyl)-3-ethylcarbodiimide. | 493/495 (M + H)⁺ 1 Cl pattern | (300MHz, DMSO-d₆)δ=3.0–3.2(m, 4H), 3.4–3.8(M, 4H), 7.25(d, 2H), 7.7(d, 1H), 7.8(d, 1H), 8.05(d, 1H), 8.1–8.3(m, 5H), 8.5(s, 1H), 8.9(d, 1H), 9.25(s, 1H)ppm |
| 4 | 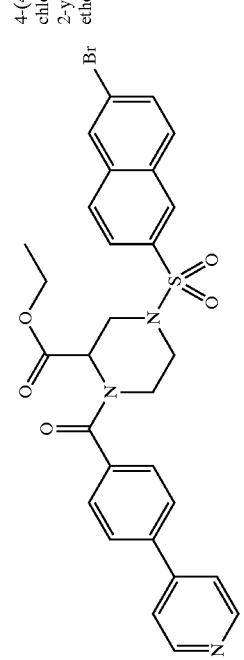 | 4-(4-pyridyl)benzoyl chloride + 4-(6-bromonaphth-2-ylsulphony-2-ethoxycarbonyl piperazine. | 608/610 (M + H)⁺ 1 Br pattern | (300MHz, CDCl₃)δ=2.6–3.2(t, 3H), 2.3–2.56 (b, 1H), 2.56–2.74(b, 1H), 3.60–3.82(m, 2H), 4.16–4.40(–4.56(m, 1H), 5.44–5.56 (b, 1H), 7.38–7.56(m, 4H), 7.56–7.70(d, 2H), 7.70–7.82(d, 2H), 7.82–7.94(m, 2H), 8.14(s, 1H), 8.32(s, 1H), 8.64–8.72(d, 2H)ppm. |

TABLE 1-continued

| No. | Compound | Method | MS:m/z | ¹H NMR (MHz, solvent) |
|---|---|---|---|---|
| 5 | (structure: 4-[4-(6-bromonaphth-2-ylsulphonyl)piperazine-1-carbonyl]phenyl linked to 3-fluoropyridin-4-yl) | 4-(3-fluoro-4-pyridyl)benzoic acid[3] + 1-(6-bromonaphth-2-ylsulphonyl)piperazine: reaction using 1-(3-dimethylaminopropyl)-3-ethylcarbodiimide. | 554/556 (M + H)⁺ 1 Br pattern | (300MHz, DMSO-d₆)δ=3.15(s, 4H), 3.48–3.88(bm, 4H), 7.57 (d, 2H), 7.68–7.80(m, 3H), 7.92 (t, 2H), 8.25(t, 2H), 8.50(s, 1H), 8.58 (m, 2H), 8.74(s, 1H)ppm. |
| 6 | (structure: 2-methoxy-4-(pyridazin-4-yl)phenyl linked via carbonyl to piperazine sulfonyl 6-bromonaphthalene) | 2-methoxy-4-(4-pyridazinyl)benzoic acid[4] + 1-(6-bromonaphth-2-ylsulphonyl)piperazine: reaction using 1-(3-dimethylaminopropyl)-3-ethylcarbodiimide. | 567/569 (M + H)⁺ 1 Br pattern | (300MHz, DMSO-d₆)δ=2.94(m, 4H), 3.22 (m, 2H), 3.63(s, 3H), 3.72(s, 2H), 7.26 (d, 1H), 7.45(d, 1H), 7.47(s, 1H), 7.82 (t, 2H), 8.02(dxd, 1H), 826(d, 1H), 8.02(d, 1H), 8.40(s, 1H), 8.48(s, 1H), 9.27(d, 1H), 9.64(m, 1H)ppm. |
| 7 | (structure: 4-(1-oxo-4-pyridyl)phenyl linked via carbonyl to piperazine sulfonyl 6-bromonaphthalene) | 4-(1-oxo-4-pyridyl)benzoic acid[5] + 1-(6-bromonaphth-2-ylsulphonyl)piperazine: reaction using 1-(3-dimethylaminopropyl)-3-ethylcarbodiimide + 1-hydroxybenztriazole. | 552/554 (M + H)⁺ 1 Br pattern | (300 MHz, CDCl₃)δ=3.15(bs, 4H), 3.75(b, 4H), 7.45(m, 4H), 7.58(d, 2H), 7.75(t, 2H), 7.85 (d, 1H), 7.92(d, 1H), 8.12(s, 1H), 8.25(d, 2H), 8.30(s, 1H)ppm. |

TABLE 1-continued

| No. | Compound | Method | MS:m/z | $^1$H NMR (MHz, solvent) |
|---|---|---|---|---|
| 8 | (structure) | 4-(2-cyano-4-pyridyl)benzoic acid[6] + 1-(6-bromonaphth-2-ylsulphonyl)piperazine: reaction using 1-(3-dimethylaminopropyl)-3-ethylcarbodiimide | 561/563 $(M + H)^+$ 1 Br pattern | (300 MHz, CDCl$_3$)δ=3.15(bs, 4H), 3.72(b, 4H), 7.46(2h, d), 7.60–7.80(m, 5H), 7.86(d, 2H), 7.93 (d, 1H), 8.13(s, 1H), 8.30(s, 1H), 8.79(s, 1H)ppm. |
| 9 | (structure) | 4-(2-amino-4-pyridyl)benzoic acid[7] + 1-(6-bromonaphth-2-ylsulphonyl)piperazine: reaction using 1-(3-dimethylaminopropyl)-3-ethylcarbodiimide | 551/553 $(M + H)^+$ 1 Br pattern | (300 MHz, DMSO-d$_6$)δ=3.06(bs, 4H), 2.20–3.80(b, 4H + H$_2$O), 7.15(s, 1H), 7.18(s, 1H), 7.49(d, 2H), 7.76(d, 2H), 7.81(t, 2H), 7.90–8.04 (m, 3H), 8.18(t, 2H), 8.40(s, 1H), 8.47(s, 1H)ppm. |
| 10 | (structure) | 1-(6-bromonaphth-2-ylsulphonyl)-4-2-carboxy-4-(4-pyridyl)benzoyl]piperazine[8] + diethanolamine: reaction using 1-(3-dimethylaminopropyl)-3-ethylcarbodiimide + 1-hydroxybenztriazole. | 667/669 $(M + H)^+$ 1 Br pattern | (300 MHz, DMSO-d$_6$ at 373° K,)δ=3.18(t, 4H), 3.31(t, 4H), 3.47(m, 8H), 7.38(d, 1H), 7.63 (dd, 2H), 7.74(m, 2H), 7.79(m, 1H), 7.82 (d, 1H), 8.08(d, 1H), 8.13(d, 1H), 8.31(d, 1H), 8.42(d, 1H), 8.63(m, 2H)ppm. |

TABLE 1-continued

| No. | Compound | Method | MS:m/z | ¹H NMR (MHz, solvent) |
|---|---|---|---|---|
| 11 | (structure: 4-pyridyl-phenyl-C(O)-piperazine-SO₂-CH=CH-(4-chlorophenyl)) | 4-(4-pyridyl)benzoic acid + 1-[(E)-4-chlorostyrylsulphonyl]piperazine⁹: reaction using 1,3-dicyclohexylcarbodiimide + 1-hydroxybenzotriazole. | 468/470 (M + H)⁺ 1 Cl pattern | (300 MHz, DMSO-d₆)δ=3.20(m, 4H), 3.65 (bs, 4H), 7.33(d, 1H), 7.46(d, 1H), 7.49(d, 2H), 7.56(d, 2H), 7.72(d, 2H), 7.81(d, 2H), 7.86 (d, 2H), 8.65(d, 2H)ppm. |
| 12 | (structure: 2-pyrimidinyl-phenyl-C(O)-N-(oxopiperazine)-SO₂-(6-bromonaphth-2-yl)) | 6-bromonaphth-2-ylsulphonyl chloride + 2-oxo-1-[4-(4-pyrimidinyl)benzoyl]piperazine¹⁰ | 552 (M + H)⁺ | (300 MHz, CDCl₃)δ=3.64(dd, 2H), 4.00 (m, 4H), 7.45(d, 2H), 7.70–7.95(m, 4H), 7.97–8.05(m, 3H), 8.18(s, 1H), 8.42(s, 1H), 8.82 (d, 1H), 9.30(s, 1H)ppm. |

¹Prepared according to the method described in Example 1 & 1 (c) starting from 2-methyl-4-chloropyrimidine
²Prepared according to the method described in Example 1 (c) starting from 2,6-dimethyl-4-chloropyrimidine and subsequent ester hydrolysis
³Prepared according to the method described in Example 1(c) starting from 3-fluoro-4-iodopyridine and subsequent ester hydrolysis
⁴Prepared according to methods described in Example 9(a) and (b) starting from methyl 4-amino-2-methoxybenzoate
⁵Prepared from 4-(4-pyridyl)benzoic acid described in Example 3(c) by esterification, then oxidation with 3-chloroperoxybenzoic acid, and subsequent ester hydrolysis.
⁶Prepared by a palladium catalysed coupling of 4-chloro-2-cyanopyridine and 4-carboxyphenylboronic acid using bis-((tri-o-tolylphosphine)palladiumchloride.
⁷Prepared by a palladium catalysed coupling of 2-(N-tert-butoxycarbonylamino)-4-bromopyridine and 4-carboxyethylphenylboronic acid using [1,1'-bis(diphenylphosphino)ferrocene]diacetylpalldium.
⁸Prepared from the ester described in Example 10 by base hydrolysis.
⁹Described in WO96/10022 Ex57 page 109 last paragraph
¹⁰Prepared by reacting 4-(4-pyrimidinyl)benzoyl chloride with 1-tert-butoxycarbonyl-3-oxopiperazine and subsequent treatment with trifluoroacetic acid.

What is claimed is:

1. A compound of formula (I)

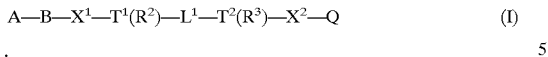

wherein:
A is 5- or 6-membered monocyclic aromatic ring containing 1, 2 or 3 ring heteroatoms selected form nitrogen, optionally substituted by one, two or three atoms or groups selected from halo, oxo, carboxy, trifluoromethyl cyano, amino, hydroxy, nitro, $C_{1-4}$alkyl, $C_{1-4}$alkoxy, $C_{1-4}$alkoxycarbonyl, $C_{1-4}$alkylamino or di-$C_{1-4}$alkylamino;

B is a phenylene ring optionally substituted by one or two substituents selected from halo, trifluoromethyl, trifluoromethoxy, cyano, nitro, $C_{1-4}$alkyl, $C_{2-4}$alkenyl and $C_{2-4}$alkynyl, from the substituent —$(CH_2)_nY^1$ wherein n is 0–4 and $Y^1$ is selected from hydroxy, amino, carboxy, $C_{1-4}$alkoxy, $C_{2-4}$alkenyloxy, $C_{2-4}$alkynyloxy, $C_{1-4}$alkylamino, di-$C_{1-4}$alkylamino, pyrrolidin-1-yl, piperidino, morpholino, thiomorpholino, 1-oxothiomorpholino, 1,1-dioxothiomorpholino, piperazin-1-yl, 4-$C_{1-4}$ alkylpiperazin-1-yl, $C_{1-4}$alkylthio, $C_{1-4}$-alkylsulphinyl, $C_{1-4}$alkylsulphonyl, $C_{2-4}$alkanoylamino, benzamido, $C_{1-4}$alkylsulphonamido and phenylsulphonamido, from the substituent —$(CH_2)_nY^2$ wherein n is 0–4 and $Y^2$ is selected from carboxy, carbamoyl, $C_{1-4}$alkoxycarbonyl, N—$C_{1-4}$alkylcarbamoyl, N,N-di-$C_{1-4}$-alkylcarbamoyl, pyrrolidin-1-ylcarbonyl, piperidinocarbonyl, morpholinocarbonyl, thiomorpholinocarbonyl, 1-oxothiomorpholinocarbonyl, 1,1-dioxothiomorpholinocarbonyl, piperazin-1-ylcarbonyl, 4-$C_{1-4}$alkylpiperazin-1-ylcarbonyl, $C_{1-4}$alkylsulphonamidocarbonyl, phenylsulphonamidocarbonyl and benzylsulphonamidocarbonyl, from a substituent of the formula —$X^3$—$L^2$—$Y^2$ wherein $X^3$ is a group of the formula $CON(R^5)$, $CON(L^2-Y^2)$, $C(R^5)_2O$, O, $N(R^5)$ or $N(L^2-Y^2)$, $L^2$ is $C_{1-4}$alkylene, $Y^2$ has any of the meanings defined immediately hereinbefore and each $R^5$ is independently hydrogen or $C_{1-4}$alkyl, and from a substituent of the formula —$X^3$—$L^3$—$Y^1$ wherein $X^3$ is a group of the formula $CON(R^5)$, $CON(L^3-Y^1)$, $C(R^5)_2O$, O, $N(R^5)$ or $N(L^3-Y^1)$, $L^3$ is $C_{2-4}$alkylene, $Y^1$ has any of the meanings defined immediately hereinbefore and each $R^5$ is independently hydrogen or $C_{1-4}$alkyl, and wherein any heterocyclic group in a substituent of B optionally bears 1 or 2 substituents selected from carboxy, carbamoyl, $C_{1-4}$alkyl, $C_{1-4}$alkoxycarbonyl, N—$C_{1-4}$alkylcarbamoyl and N,N-di-$C_{1-4}$alkylcarbamoyl, and wherein any phenyl group in a substituent of B optionally bears 1 or 2 substituents selected from halo, trifluoromethyl, cyano, $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy;

$T^1$ and $T^2$ are N, $L^1$ is ethylene, and $R^2$ and $R^3$ are joined to form an ethylene such that $R^2$ and $R^3$, together with $T^1$ and $T^2$ and $L^1$, form a piperazine ring;

wherein the heterocyclic ring formed by $T^1$, $T^2$, $L^1$, $R^2$ and $R^3$ is optionally substituted by one or two substituents selected from hydroxy, oxo, carboxy and $C_{1-4}$alkoxycarbonyl; or one of the following:

—$(CH_2)_n$—R, —$(CH_2)_n$—$NRR^1$, —CO—R, —CO—$NRR^1$, —$(CH_2)_n$—CO—R and —$(CH_2)_n$—CO—$NRR^1$;

wherein n is 0, 1 or 2, preferably n is 1 or 2;

R and $R^1$ are independently selected from hydrogen, $C_{1-4}$alkyl, $C_{2-4}$alkenyl, $C_{2-4}$alkynyl, hydroxy$C_{1-4}$ alkyl, carboxy$C_{1-4}$alkyl and $C_{1-4}$alkoxycarbonyl$C_{1-4}$ alkyl or where possible R and $R^1$ may together form a 5- or 6-membered optionally substituted saturated or partially unsaturated heterocyclic ring which may include in addition to the nitrogen to which R and $R^1$ are attached 1 or 2 additional heteroatoms selected from nitrogen, oxygen and sulphur;

$X^1$ is SO, $SO_2$, $C(R^4)_2$ or CO, wherein each $R^4$ is independently hydrogen or $C_{1-4}$alkyl;

$X^2$ is $S(O)_y$ wherein y is one or two, $C(R^5)_2$ or CO; and each $R^5$ is hydrogen or $C_{1-4}$alkyl;

Q is phenyl, naphthyl, phenyl$C_{1-4}$alkyl, phenyl$C_{2-4}$alkenyl, phenyl$C_{2-4}$alkynyl or a heterocyclic moiety containing up to 4 heteroatoms selected from nitrogen, oxygen and sulphur and Q is optionally substituted by one, two or three substituents selected from halo, trifluoromethyl, trifluoromethoxy, cyano, hydroxy, amino, nitro, trifluoromethylsulphonyl, carboxy, carbamoyl, $C_{1-4}$alkyl, $C_{2-4}$alkenyl, $C_{2-4}$alkynyl, $C_{1-4}$alkoxy, $C_{2-4}$alkenyloxy, $C_{2-4}$alkynyloxy, $C_{1-4}$alkylthio, $C_{1-4}$alkylsulphinyl, $C_{1-4}$alkylsulphonyl, $C_{1-4}$alkylamino, di-$C_{1-4}$alkylamino, $C_{1-4}$-alkoxycarbonyl, N—$C_{1-4}$alkylcarbamoyl, N,N-di-$C_{1-4}$alkylcarbamoyl, $C_{2-4}$alkanoyl, $C_{2-4}$-alkanoylamino, hydroxy$C_{1-4}$alkyl, $C_{1-4}$alkoxy$C_{1-4}$ alkyl, carboxy$C_{1-4}$alkyl, $C_{1-4}$-alkoxycarbonyl$C_{1-4}$ alkyl, carbamoyl$C_{1-4}$alkyl, N—$C_{1-4}$ alkylcarbamoyl$C_{1-4}$alkyl, N,N-di-$C_{1-4}$-alkylcarbamoyl$C_{1-4}$alkyl, phenyl, heteroaryl, phenoxy, phenylthio, phenylsulphinyl, phenylsulphonyl, benzyl, benzoyl, heteroaryloxy, heteroarylthio, heteroarylsulphinyl and heteroarylsulphonyl, and wherein said heteroaryl substituent or the heteroaryl group in a heteroaryl-containing substituent is a 5- or 6-membered monocyclic heteroaryl ring containing up to 3 heteroatoms selected from nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2 or 3 substituents selected from halo, trifluoromethyl, cyano, hydroxy, amino, nitro, carboxy, carbamoyl, $C_{1-4}$alkyl, $C_{1-4}$alkoxy, $C_{1-4}$alkylamino, di-$C_{1-4}$alkylamino, $C_{1-4}$alkoxycarbonyl, N—$C_{1-4}$alkylcarbamoyl, N,N-di-$C_{1-4}$alkylcarbamoyl and $C_{2-4}$alkanoylamino;

or a pharmaceutically acceptable salts thereof.

2. A compound of formula (I) according to claim 1 wherein A is a pyridyl, pyrimidinyl or pyridazinyl ring.

3. A compound of formula (I) according to claim 2 wherein A is 4-pyrimidinyl or 4-pyridyl.

4. A compound of formula (I) according to claim 1 wherein B is paraphenylene.

5. A compound of formula (I) according to claim 1 wherein the ring formed by $T^1$, $R^2$, $R^3$, $T^2$ and L is 1,4-piperazinediyl.

6. A compound of formula (I) according to claim 1 wherein $X^1$ is CO.

7. A compound of formula (I) according to claim 1 wherein $X^2$ is $SO_2$.

8. A compound of formula (I), according to claim 1, wherein

A is pyridyl, pyrimidinyl, or pyridazinyl;
B is para-phenylene;
$X^1$ is CO, $SO_2$ or $CH_2$;
—$T^1(R^2)$—$L^1$—$T^2(R^3)$—forms a piperazine ring;
$X^2$ is $SO_2$;
Q is styryl or naphthyl optionally substituted by fluoro, chloro or bromo or is phenyl optionally substituted by fluorophenyl, chlorophenyl, or bromophenyl;
or a pharmaceutically-acceptable salts thereof.

9. A pharmaceutical formulation comprising a compound of formula (I) according to any one of claims 1 to 8 and a pharmaceutically-acceptable diluent or carrier.

10. A method of preventing or treating a Factor Xa mediated disease or medical condition comprising administering to a patient a pharmaceutically effective amount of a compound of formula (I), as defined in any one of claims 1 to 8.

11. A process for preparing a compound of formula (I), are defined in claim 1, comprising:

(a) for the production of those compounds of the formula (I) wherein $T^1$ is N and $X^1$ is CO, the reaction, conveniently in the presence of a suitable base, of an amine of formula (II)

$$HN(R^2)—L^1—T^2(R^3)—X^2—Q \quad (II)$$

with an acid of the formula (III)

$$A—B—COOH \quad (III)$$

or a reactive derivative thereof;

(c) for the production of those compounds of the formula (I) wherein $T^1$ is N and $X^1$ is $CH(R^4)$, the reductive amination of a keto compound of the formula (VI):

$$A—B—CO—R^4 \quad (VI)$$

wherein $R^4$ is hydrogen or $C_{1-4}$alkyl, with an amine of the formula (II) as defined above;

(d) the reaction of a compound of the formula (VII):

$$Z—B—X^1—T^1(R^2)—L^1—T^2(R^3)—X^2—Q \quad (VII)$$

wherein Z is a displaceable group with an activated derivative of ring A;

(e) by forming A ring on compounds of formula (VII), wherein Z is a functional group capable of cyclisation;

(f) for the production of compounds wherein $T^2$ is N, the reaction of a compound of the formula (VIII):

$$A—B—X^1—T^1(R^2)—L^1—NH(R^3) \quad (VIII)$$

with a compound of the formula (IX):

$$Z—X^2—Q \quad (IX)$$

wherein Z is a displaceable group;

(g) for the production of compounds wherein $T^1$ is N and $X^1$ is SO or $SO_2$, the reaction of a compound of the formula (II) as defined above with a compound of the formula (X):

$$A—B—SO_x—Z \quad (X)$$

wherein x is one or two and Z is a displaceable group;

(h) for production of compounds of formula (I) by coupling $T^2$ to Q and thus preparing the —$T^2$—$X^2$—Q moiety, methods analogous to those described in process variants (a), (c) and (g) for preparing the B—$X^1$—$T^1$— moiety may be employed;

(i) for the production of compounds of formula (I) wherein $X^1$ is a group of the formula SO, $SO_2$, wherein B bears a $C_{1-4}$alkylsulphinyl, $C_{1-4}$alkylsulphonyl, 1-oxothiomorpholino or 1,1-dioxothiomorpholino group, wherein $X^2$ is a group of the formula SO or $SO_2$, wherein Q bears a $C_{1-4}$alkylsulphinyl, $C_{1-4}$alkylsulphonyl, phenylsulphinyl, phenylsulphonyl, heteroarylsulphinyl or heteroarylsulphonyl group, the oxidation of the corresponding compound of the formula (I) which contains $X^1$ as a thio group.

* * * * *